US012582691B2

(12) United States Patent
Xing et al.

(10) Patent No.: US 12,582,691 B2
(45) Date of Patent: Mar. 24, 2026

(54) ADMINISTRATION OF YUNNAN BAIYAO OR XINGNAOJING IN PATIENTS WITH MODERATE-TO-SEVERE TRAUMATIC BRAIN INJURY AND CRANIOTOMY

(71) Applicant: Lotus Biotech.com LLC, Gaithersburg, MD (US)

(72) Inventors: Guoqiang Xing, Gaithersburg, MD (US); Xiaodong Ma, Beijing (CN)

(73) Assignee: Lotus Biotech.com LLC, Gaithersburg, MD (US)

( * ) Notice: Subject to any disclaimer, the term of this patent is extended or adjusted under 35 U.S.C. 154(b) by 385 days.

(21) Appl. No.: 17/812,171

(22) Filed: Jul. 12, 2022

(65) Prior Publication Data

US 2023/0024831 A1 Jan. 26, 2023

Related U.S. Application Data

(60) Provisional application No. 63/220,936, filed on Jul. 12, 2021.

(51) Int. Cl.
| | |
|---|---|
| *A61K 36/9066* | (2006.01) |
| *A61K 35/55* | (2015.01) |
| *A61K 36/258* | (2006.01) |
| *A61K 36/744* | (2006.01) |
| *A61P 7/04* | (2006.01) |
| *A61P 29/00* | (2006.01) |

(52) U.S. Cl.
CPC .......... *A61K 36/9066* (2013.01); *A61K 35/55* (2013.01); *A61K 36/258* (2013.01); *A61K 36/744* (2013.01); *A61P 7/04* (2018.01); *A61P 29/00* (2018.01)

(58) Field of Classification Search
CPC .. A61K 36/9066; A61K 35/55; A61K 36/258; A61K 36/744; A61K 45/06; A61P 7/04; A61P 29/00
See application file for complete search history.

(56) References Cited

FOREIGN PATENT DOCUMENTS

CN          102247573 B    *  12/2015

OTHER PUBLICATIONS

Internal Arts International, The Many Uses of Yunnan Baiyao (Yunnan Paiyao), 2016. Retrieved online from: <https://www.internalartsinternational.com/free/many-uses-yunnan-baiyao-yunnan-paiyao-essential-part-chinese-first-aid-medicine/>. Retrieved on: Aug. 22, 2024 (Year: 2016).*

Ma, X, Yang, YX, Chen, N, Xie, Q, Wang, T, He, X, Wang, J, Meta-Analysis for Clinical Evaluation of Xingnaojing Injection for the Treatment of Cerebral Infarction, 2017, Frontiers in Pharmacology. 8:485. (Year: 2017).*

Kleindienst, A and Bullock, MR, A Critical Analysis of the Role of Neurotrophic Protein S100B in Acute Brain Injury, 2006, J Neurotrauma. 23(8):1185-1200. (Year: 2006).*

Tarudji, AW, Miller, HA, Curtis, ET, Porter, CL, Madsen, GL, Kievit, FM, Sex-based differences of antioxidant enzyme nanoparticle effects following traumatic brain injury, 2023, J Controlled Release. 355:149-159. (Year: 2023).*

Oris, C, Kahouadji, S, Durif, J, Bouvier, D, Sapin, V, S100B, Actor and Biomarker of Mild Traumatic Brain Injury, 2023, Int J Molecular Sciences. 24:6602. (Year: 2023).*

Peterfreund, R.A. and Philip, J.H., Critical parameters in drug delivery by intravenous infusion, 2013, Expert Opinion on Drug Delivery, 10(8):1095-1108, 15 pages. <https://doi.org/10.1517/17425247.2013.785519>. (Year: 2013).*

Yunnan Baiyao USA, Yunnan Baiyao Core Ingredients, 2023, 13 pages. Available online: <https://yunnanbaiyaousa.com/blog/yunnan-baiyao-core-ingredients/>. (Year: 2023).*

Zhang, Y., et al., Xingnaojing Injection Protects against Cerebral Ischemia Reperfusion Injury via PI3K/Akt-Mediated eNOS Phosphorylation, 2018, Evidence-Based Complementary and Alternative Medicine, 2361046, 13 pages. <https://doi.org/10.1155/2018/2361046>. (Year: 2018).*

Lu, Z., Protecting Tradition, 2005, China Daily, 2 pages. Available online: <https://www.chinadaily.com.cn/english/doc/2005-10/10/content_483570.htm>. (Year: 2005).*

* cited by examiner

*Primary Examiner* — Aaron J Kosar
*Assistant Examiner* — Jennifer Lynn Cain
(74) *Attorney, Agent, or Firm* — Syncoda LLC; Feng Ma

(57) ABSTRACT

Clinically validated methods of administering Yunnan Baiyao or Xingnaojing can improve postoperative recovery and long-term clinical prognosis of patients with moderate-to-severe traumatic brain injury (TBI) and emergency craniotomy. Both medicinal methods are useful for minimizing or inhibiting the adverse impacts of secondary injury, oxidative damage and neuroinflammation associated with TBI, spinal cord injury, craniotomy/craniectomy, cerebral hemostasis and hemorrhage, coagulopathy, stroke, neural injury and neuroinflammation, and for promoting the long-term functional recovery and well-being of the patients with the afore-mentioned diseases.

7 Claims, 11 Drawing Sheets

Flow Diagram of enrollment, intervention and follow up of patients with moderate-to-severe TBI and craniotomy

ADMINISTRATION OF YUNNAN BAIYAO OR XINGNAOJING IN PATIENTS WITH MODERATE-TO-SEVERE TRAUMATIC BRAIN INJURY AND CRANIOTOMY

CROSS-REFERENCE TO RELATED APPLICATION

This application claims priority to U.S. Provisional Patent Application No. 63/220,936, filed on Jul. 12, 2021, the disclosure of which is hereby incorporated by reference in its entirety.

BACKGROUND

Secondary brain injury following Traumatic brain injury (TBI) is currently the main target for therapeutic intervention. TBI is a complex and diffuse injury with multi-modes of lesions, including focal cerebral contusion, parenchymal laceration, hemorrhages (subdural, epidural, and/or subarachnoid), diffuse axonal injury, diffuse hypoxic-ischemic insults, cerebral swelling, increased intracranial pressure and brain compression and herniation. Adjacent brain tissues that are not destroyed immediately following the primary injury often experience sub-acute injury or delayed death caused by secondarily generated auto-destructive factors. Blood S100B protein is a glial-derived, brain specific calcium-binding protein that are highly elevated after TBI. High concentration of S100B overproduced by injured astrocytes after TBI exacerbates neurovascular inflammatory responses and apoptosis through interaction with the receptor for advanced glycation end products (RAGE). Serum S100B protein is a reliable biomarker of TBI severity and secondary brain injury. Extracellular Superoxide Dismutase (SOD) is the only extracellular scavenger responsible for scavenging reactive oxygen species (ROS) which are major causes of oxidative damage and secondary injury of TBI. Depletion in SOD activity and antioxidant function of the body have been reported in TBI, and is linked to increased risk or poor prognosis of acute injury and organs failure. Although orthodox treatments (OT) such as hyperosmolar therapy, sedation, barbiturate coma, hypothermia therapy and ventricular drainage have been used in TBI management, they are often not effective. Surgical removal of intracranial hematoma and fractured brain tissue (craniotomy/decompression craniectomy) can reduce the mortality of severe TBI, incidence of ICP, and length of hospital stay in TBI patients (Rutigliano et al., 2006; Shim et al., 2018; Lu et al., 2020). Surgery, however, could also worsen the clinical outcomes of TBI (Qiu et al., 2009; Su et al., 2019), partly due to secondary injury, increased bleeding and inflammatory complications (Muller et al., 1988; Tapper et al., 2017; Cheng et al., 2018, Raso Vasquez et al., 2018, Glass et al., 2019, Lu et al., 2020). Timely appropriate drug treatment after craniotomy could potentially reduce secondary injuries and improve the prognosis of TBI. So far, all experimental drugs for treatment of TBI failed in clinical trials. Recent evidence suggests that complementary and alternative medicine (CAM) may benefit the clinical outcomes of TBI. Yunnan Baiyao (YB) is a traditional hemostatic drug for wound healings. Until now, its efficacy for postoperative TBI has not been evaluated due to the technical difficulty/complexity, high cost, and high risk associated with clinical trial of TBI. Xingnaojing (XNJ) is an intravenous formula based on the traditional medicine Angong Niuhuang Pill (ANP). To date, the utility and effectiveness of administration of YB and XNJ as the neuroprotectant and anti-neuroinflammation agents in patients with traumatic brain injury (TBI) and craniotomy have remained unexplored. The Glasgow Coma Scale (GCS) is used to evaluate disturbance of consciousness with eye opening, speech condition and motor response (mild=13-15, moderate=8-12, severe=3-7). The Glasgow Outcome Scale (GOS) and Karnofsky Performance Scale (KPS) are scales performed to evaluate long-term clinical prognosis of TBI.

SUMMARY

Described herein is a method having many attributes and embodiments including, but not limited to, that set forth or described in this brief summary. It is not intended to be all-inclusive and the claims are not limited to or by the features or embodiments identified in this brief summary.

The present disclosure relates to the neuroprotection and neurotherapies by two complementary and alternative medicines Yunnan Baiyao (also termed "YB") and Xingnaojing (also termed "XNJ") in patients with moderate-to-severe traumatic brain injury (TBI) and emergency craniotomy. The present disclosure pertains to the discovery of novel therapies for neurodegeneration and/or neuroinflammation-related brain neuropathies, including spinal cord injury, brain tumor, ischemia stroke and cerebrohemorrhage, and methods for preventing the secondary-injuries of craniotomy operations on these disorders.

Accordingly, in one aspect, the present disclosure is directed to the novel and significant inhibitory activities of orally administered or stomach-tube administered YB, on TBI-induced increase in blood S100B level during the acute phase of postoperative TBI, demonstrating a significant neuroprotection and anti-neuroinflammation activities of YB against secondary brain injuries in patients with moderate-to-severe TBI and craniotomy.

In another aspect, the present disclosure is directed to the novel and significant protection against TBI-induced depletion of blood SOD activity during the acute phase of moderate-to-severe TBI and craniotomy by orally-administered or stomach tube-administered YB. SOD is a biomarker of body oxidative potential against TBI-induced damage.

In another aspect, the present disclosure is directed to the novel and significant inhibitory activities of intravenously-administered XNJ on TBI-induced increase in blood S100B level during the acute phase of postoperative TBI, demonstrating a significant neuroprotection and anti-neuroinflammation activity of XNJ against secondary brain injuries in patients with moderate-to-severe TBI and craniotomy.

In another aspect, the present disclosure is directed to the novel and significant protecting activity of intravenously-administered XNJ against TBI-induced depletion of blood SOD activity and therefore, XNJ preserved body anti-oxidative potential against TBI-induced oxidative damage during the acute phase of moderate-to-severe TBI and craniotomy.

In another aspect, the present disclosure is directed to the significant improvement in GCS score and therefore a more rapid recovery from coma by orally- or stomach tube-administered YB during the acute phase of TBI in patients with moderate-to-severe TBI and craniotomy.

In another aspect, the present disclosure is directed to the significant improvement in GCS score and therefore a more rapid recovery from coma after intravenous administration of XNJ during the acute phase of TBI in patients with moderate-to-severe TBI and craniotomy.

In another aspect, the present disclosure is directed to the significant improvement in 30- and 90-days Glasgow Outcome Scale (GOS) and Karnofsky Performance Scale (KPS) in TBI patients who received YB administrations during the acute phase of TBI, therefore, demonstrating improved long-term recovery in physical strength, functional rehabilitation and the abilities of daily life and work by YB.

In another aspect, the present disclosure is directed to the significant improvement in Glasgow Outcome Scale (GOS) and Karnofsky Performance Scale (KPS) at 30-days and 90-days post craniotomy in TBI patients who received intravenous XNJ during the acute phase of TBI, therefore, demonstrating improved and sustained long-term recovery by XNJ in physical strength, functional rehabilitation and the abilities of daily life and work.

In another aspect, the present disclosure is directed to the significant correlations between the acute phase GCS scores and chronic phase GOS/KPS scores in pooled TBI patients, therefore, demonstrating that a more rapid recovery during the acute phase of TBI is a predictor of more favorable long-term clinical prognosis of patients with TBI and craniotomy.

In another aspect, the present disclosure is directed to the findings that serum S100B levels were negatively correlated with GCS/GOS/KPS scores in patients with moderate-to-severe TBI and craniotomy. Because GCS reflects acute phase recovery whereas GOS/KPS reflect long-term prognosis, reduced serum S100B during the acute phase of TBI in patients administered with YB or XNJ would predict more favorable clinical outcomes of both short-term and long-term. This study also demonstrates that a higher S100B level at admission or at postoperative day 7 was s a predictor of poor TBI outcomes (low GCS/GOS/KPS scores).

In another aspect, the present disclosure is directed to the findings that serum S100B levels were negatively correlated with GCS/GOS/KPS scores in pooled patients and in different treatment groups. Because GCS predict acute phase recovery whereas GOS/KPS predict long-term prognosis, the reduced serum S100B during the acute phase of TBI in patients administered with YB or XNJ would predict their long-term clinical outcome. This study demonstrated that serum S100B levels either at admission day or at postoperative day could be a good biomarker in evaluating the therapeutic effects of novel therapies in the outcomes of TBI.

In one aspect, the present disclosure is directed to serum SOD activity which was positively correlated with GCS/GOS/KPS scores (p<0.01) in the pooled and in the 3 treatment groups but not in the OT group. Serum SOD level on postoperative Day 7 was a better predictor of GCS/GOS/KPS scores than SOD measured on other days in the pooled and 3 adjuvant treatment groups but not in the OT group, demonstrating that high level of serum SOD activity was a positive predictor of TBI clinical prognosis.

In one aspect, the present disclosure directs to the similar therapeutic effects between the two different doses of YB (1 or 2 g/day) and the intravenous dose of XNJ (20 ml/day) in patients with moderate-to-severe TBI and craniotomy, demonstrating a lower dose of YBY (1 g/day) was adequate to generate most of the beneficial effects of the higher dose of YB (2 g/day) or the intravenous XNJ (20 ml/day). Whereas intravenous XNJ would be an option for TBI patients in coma.

BRIEF DESCRIPTION OF THE DRAWINGS

FIG. 3A illustrates the GCS scores and shows that GCS score was lowest on admission in all groups but improved more quickly and became significantly greater in XNJ, L-YB, h-YB groups than in OT group on Days 3, 5 and 7 (p<0.01); FIG. 3B illustrates changes in the GCS scores and the improvement in GCS and; FIG. 3C illustrates changes in the GCS scores and that rate of improvement (%) in GCS were significantly greater in XNJ, L-YB, h-YB groups than in OT group after 3, 5 and 7 days of emergency craniotomy (p<0.01) and greater in h-YB than in L-YB and XNJ groups after 3, 5 and 7 days of emergency craniotomy (p<0.05, all); FIG. 3D illustrates serum S100B protein concentrations and shows that S100B concentration increased quickly after admission and peaked in all groups on Days 3 before it fell more rapidly and became significantly lower (p<0.01) in the XNJ, L-YB and h-YB groups than in the OT group after 3, 5 and 7 days of emergency craniotomy; FIG. 3E illustrates changes in the S100B, FIG. 3F illustrates that increases and percentage increase in serum S100B was significantly greater (p<0.01) in OT than in XNJ and h-YB groups on Day 3 whereas reduction and reduction rate was significantly greater in XNJ, L-YB and h-YB groups than in OT group after 5 and 7 days of emergency craniotomy; FIG. 3G illustrates serum SOD activities; FIG. 3H illustrates changes in SOD activities; and FIG. 3I shows that SOD activity declined rapidly after craniotomy and reached nadir on Days 3 day in all groups with a greater reduction found in OT group (38.3%) than in XNJ, L-YB and h-YB groups (16.7%, 23.4% and 20.7%) before increased more rapidly and became significantly higher in the XNJ, L-YB and h-YB groups than in the OT group after 3, 5 and 7 days of emergency craniotomy (p<0.01). By Days 7, XNJ, L-YB and h-YB groups resumed more of the baseline SOD activities (99.5%, 91.8% and 94.8%, respectively) than OT group (69.2%) (p<0.01). *, p<0.05, ** p<0.01 vs. OT; a, p<0.05, aa, p<0.01 vs. XNJ; b, p<0.05, bb, p<0.01 vs. L-YB.

DETAILED DESCRIPTION

The present disclosure involves the clinic exploration and validation of the therapeutic effects of orally-administered high and low doses ((1 or 2 g/day) of YB and intravenously-administered XNJ (20 ml/day) during the acute phase of TBI for 7 days in comparison with those of OT intervention alone, on post-surgery recovery, secondary brain injury, long-term clinical prognosis and functional recovery of patients with moderate-to-severe TBI and emergency craniotomy, based on the differences and postoperative changes in Glasgow Coma Scale (GCS), serum S100 level, serum SOD activity, Glasgow Outcome Scale (GOS), and Karnofsky Performance Scale (KPS) between the four treatment groups (OT, h-YB, I-YB and XNJ) measured at baseline, 7-, 30- and 90-days post-surgery, respectively.

The present disclosure involves the exploration of the effectiveness of YB and XNJ administration on the outcome of secondary brain injury measured by changes in serum levels of S100B and superoxide dismutase (SOD) activity. Both YB and XNJ therapies improved the acute recovery and long-term clinical prognosis of TBI and craniotomy, in part, by protecting glial cell from TBI-induced S100B overexpression and the associated secondary injury and by preserving and more rapid restoring of lost body SOD antioxidative after TBI. S100B is a brain- and glial-specific calcium-binding protein that promote neuronal survival at low concentration but exacerbates neurovascular inflammatory responses and apoptosis at high concentration induced after TBI. Serum S100B protein is a validated biomarker of TBI severity. Others reported that postoperative serum s100B levels predicted ongoing brain damage after meningioma surgery. Elevated serum S100B is a predictive index of overall injury and prognosis after trauma/surgery. Extracellular superoxide dismutase (SOD) is the only extracellular scavenger of superoxide anion ($O_2 \cdot^-$) and radicals which are major causes of oxidative damage and secondary injury of TBI. Serum SOD activity reflects the body's defense capability against free radicals-induced neural damage. Massive production and release of superoxide and radicals after TBI can cause artery dilation, edema and hemostasis whereas SOD can dose-dependently scavenge excess superoxide anion, reduce brain edema and attenuates acute brain injury after subarachnoid hemorrhage.

Figure 2:
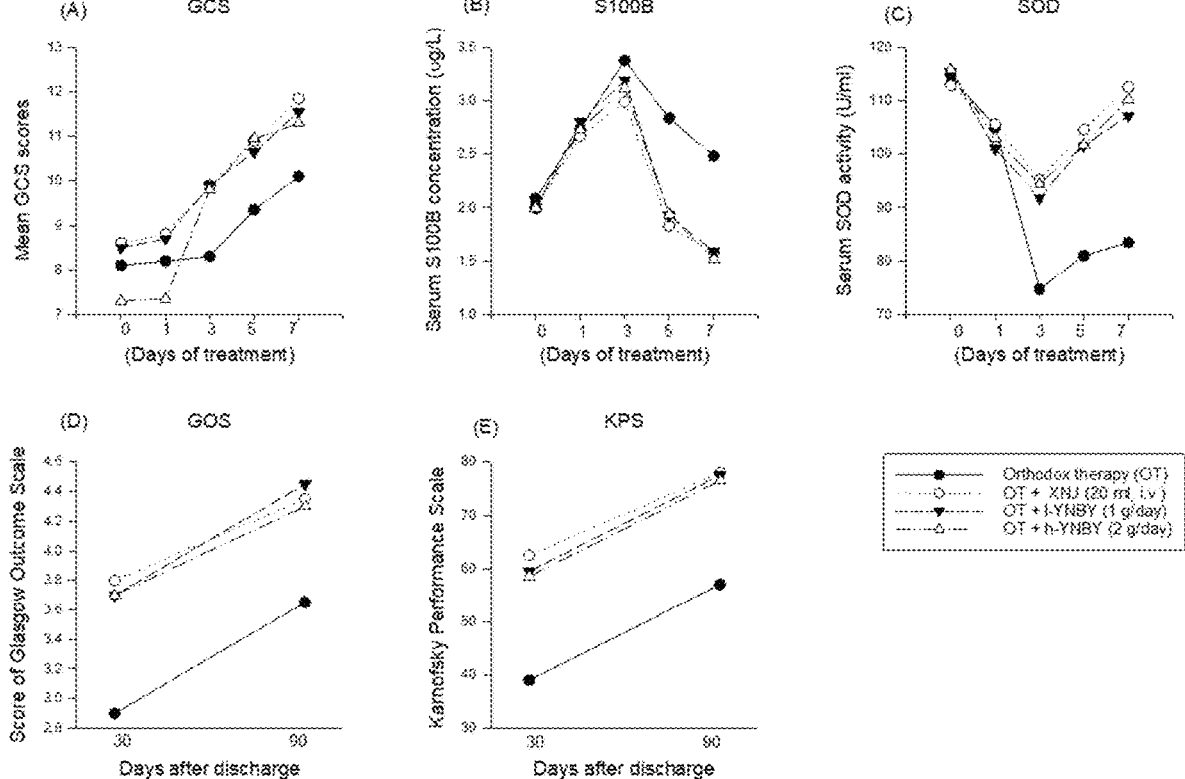
FIG. 2 is the repeated-measure analysis demonstrating significant and different impacts of 7-days treatment of orthodox therapy (OT), intravenous Xingnaojing (XNJ), low-dose Yunnan Baiyao (I-YB, 1,000 mg/day) or high-dose Yunnan Baiyao (h-YB, 2,000 mg/day) on: (A) Glasgow Coma Scale (GCS); (B) Serum S100B concentration; (C) Serum superoxide dismutase (SOD) activity; (D) Glasgow Outcome Scale (GOS) and; (E) Karnofsky Performance Scale (KPS), in patients with acute moderate-to-severe TBI and emergency craniotomy.
Figure 3A:
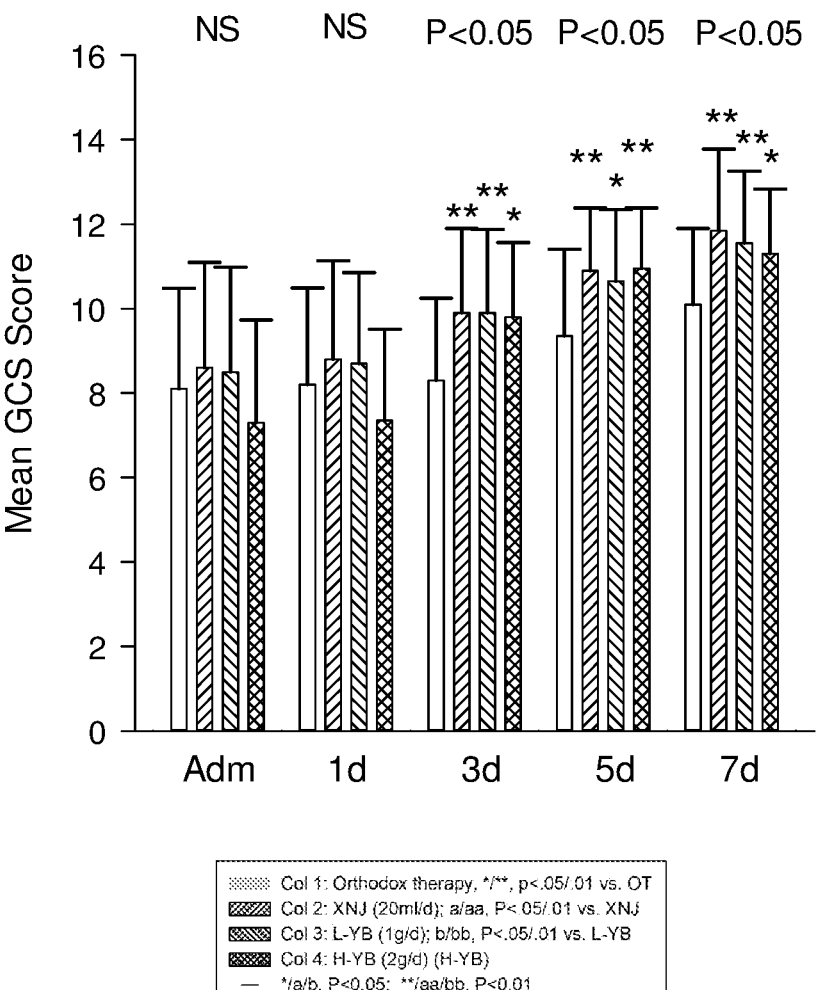
FIGS. 3A, 3B, 3C, 3D, 3E, 3F, 3G, 3H, and 3I show significant differences in GSC, serum S100B and SOD between the 4 treatment groups, where
Figure 3B:
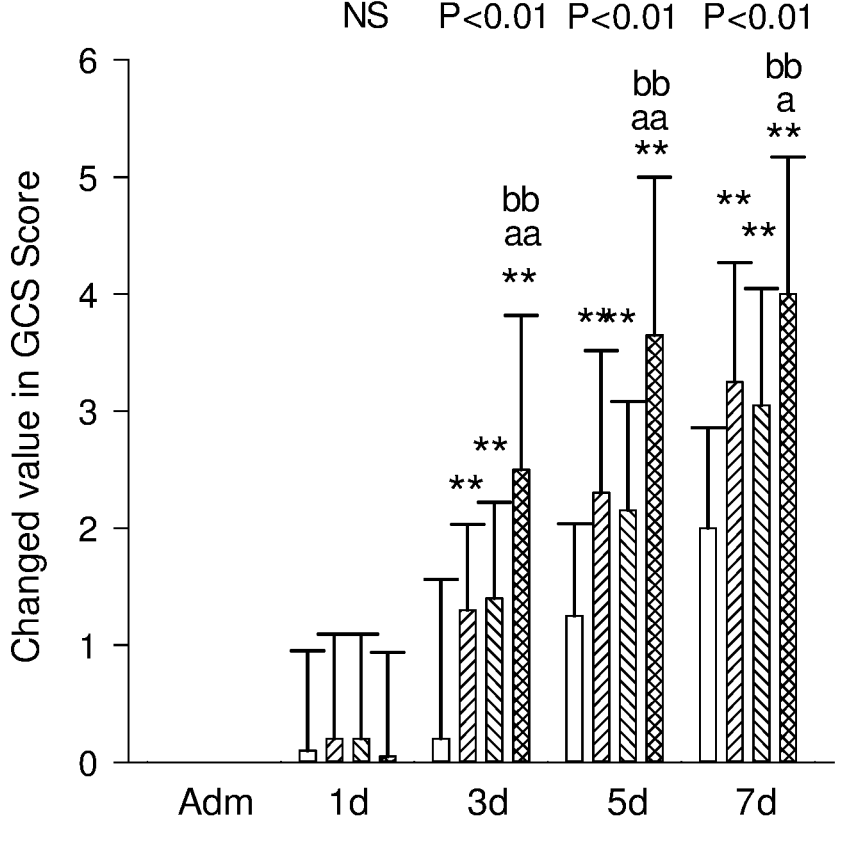
Figure 3C:
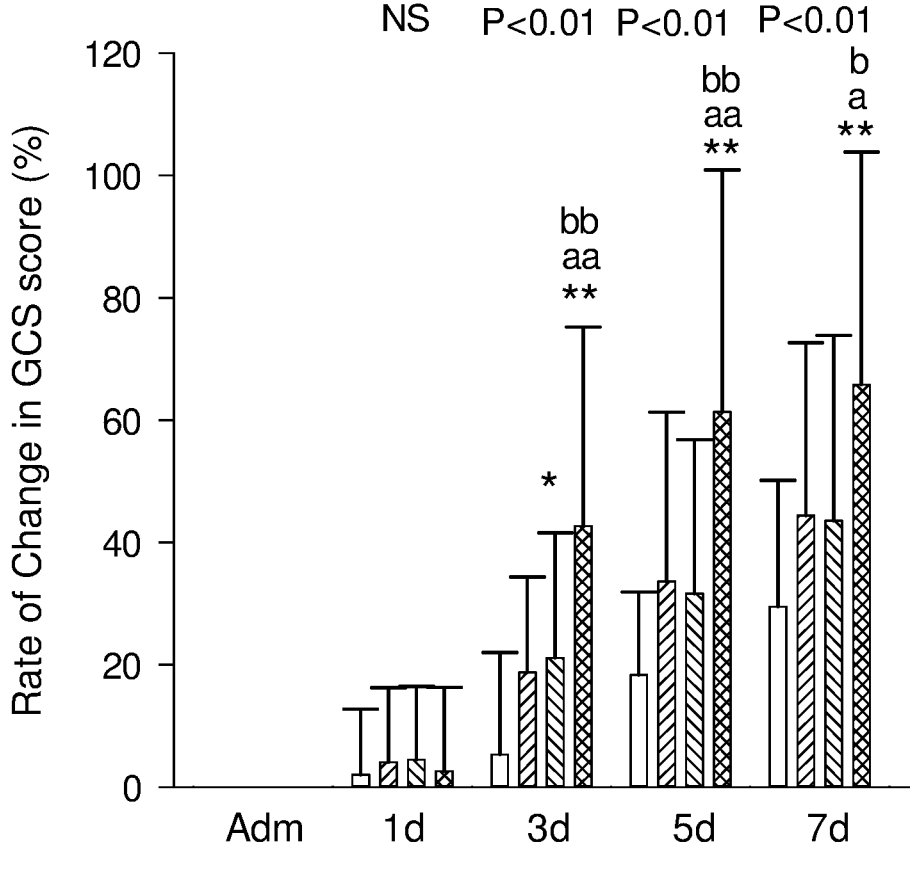
Figure 3D:
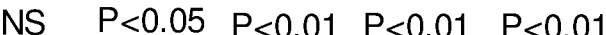
Figure 3D:
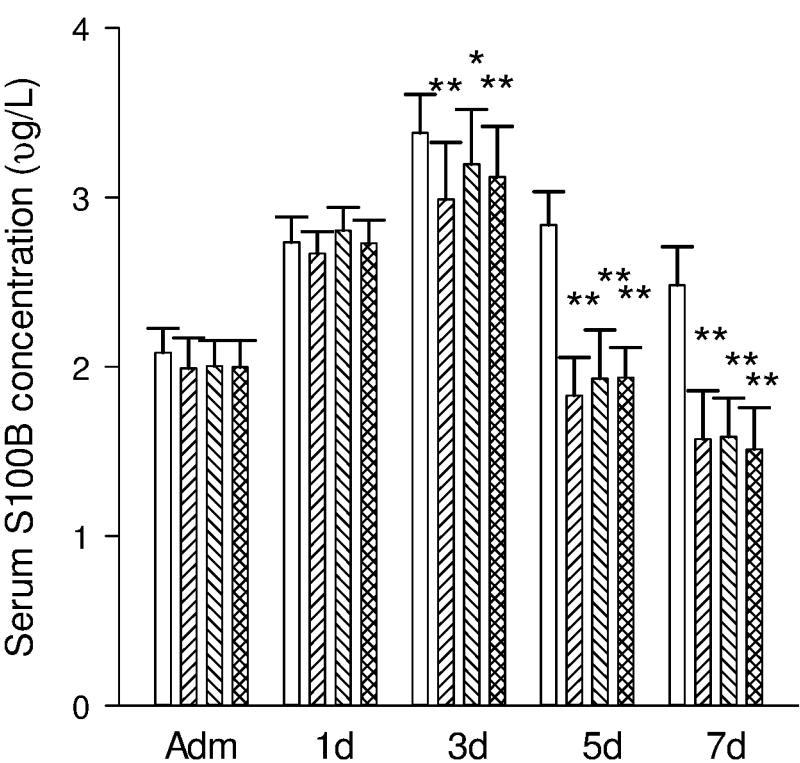
Figure 3D:
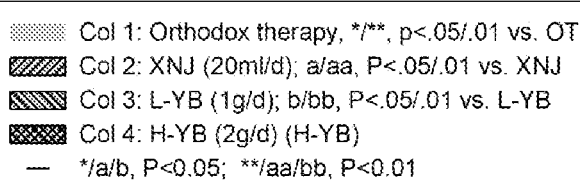
Figure 3E:
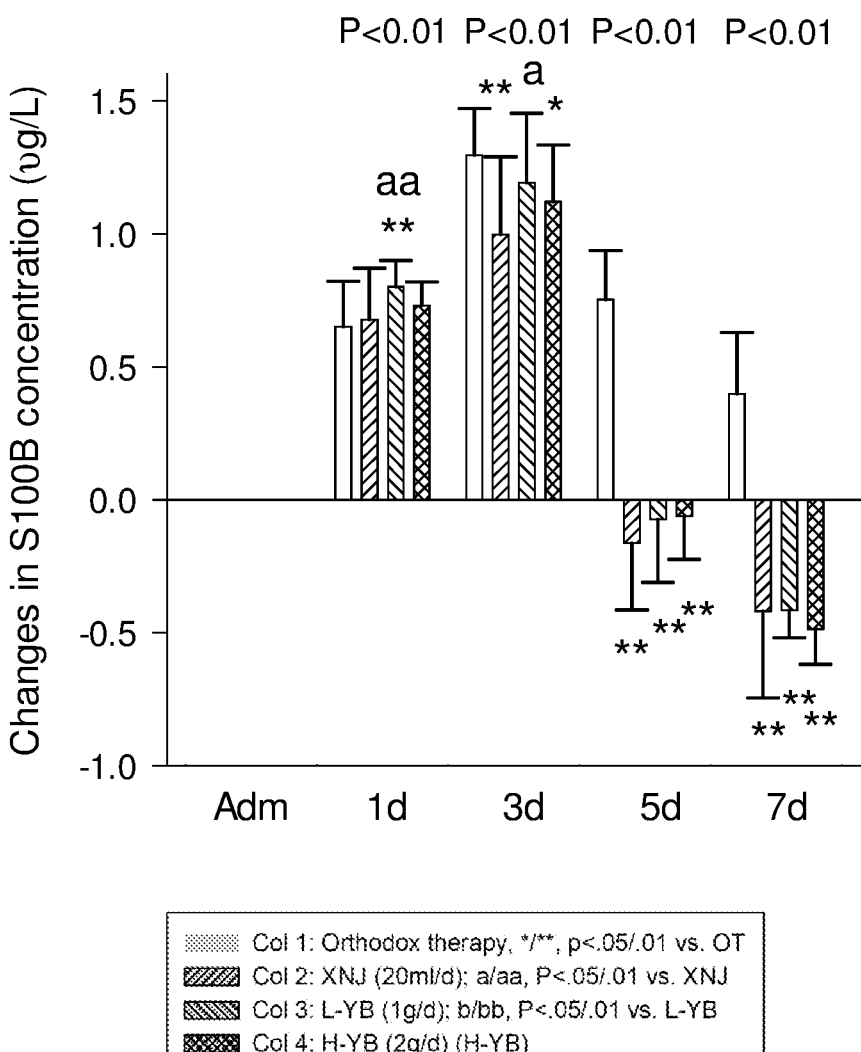
Figure 3F:
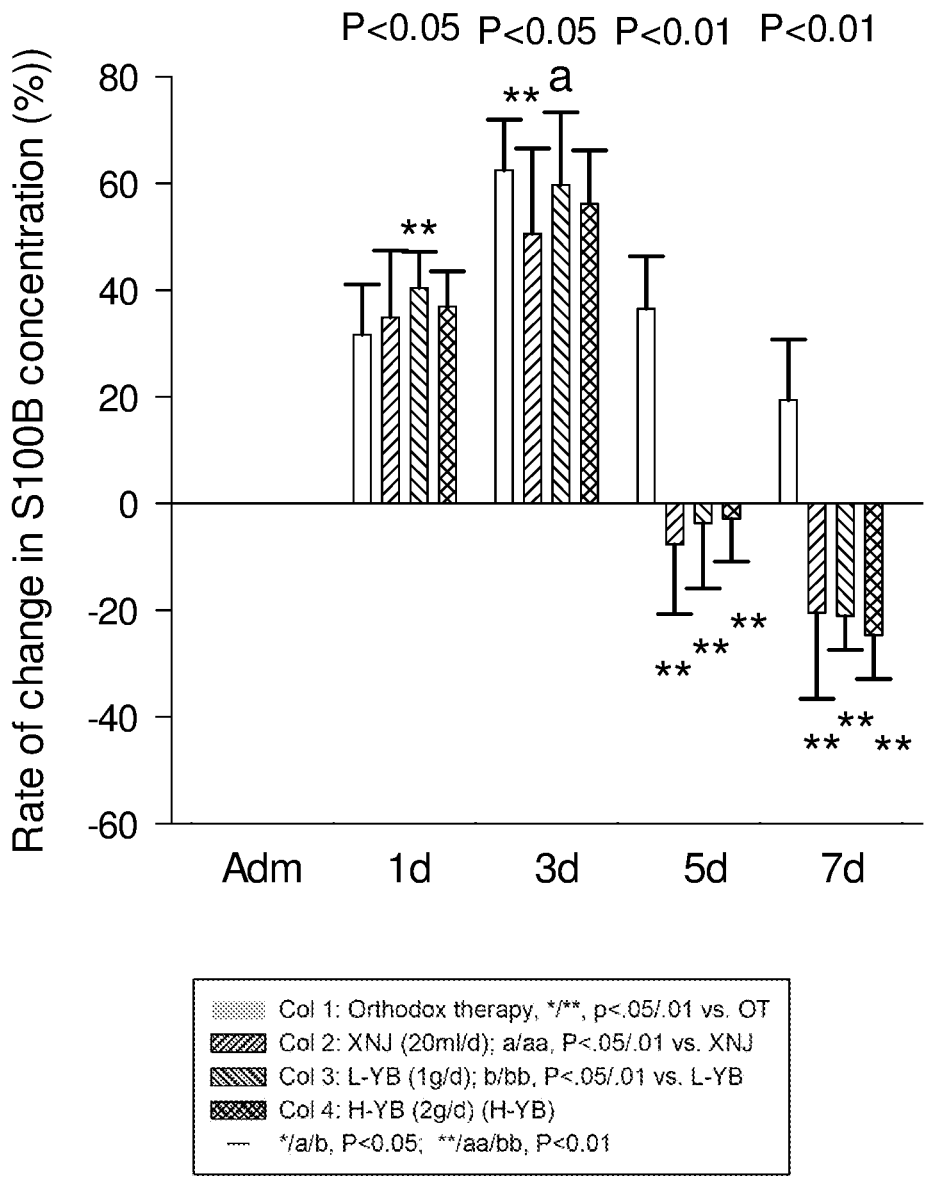
Figure 3G:
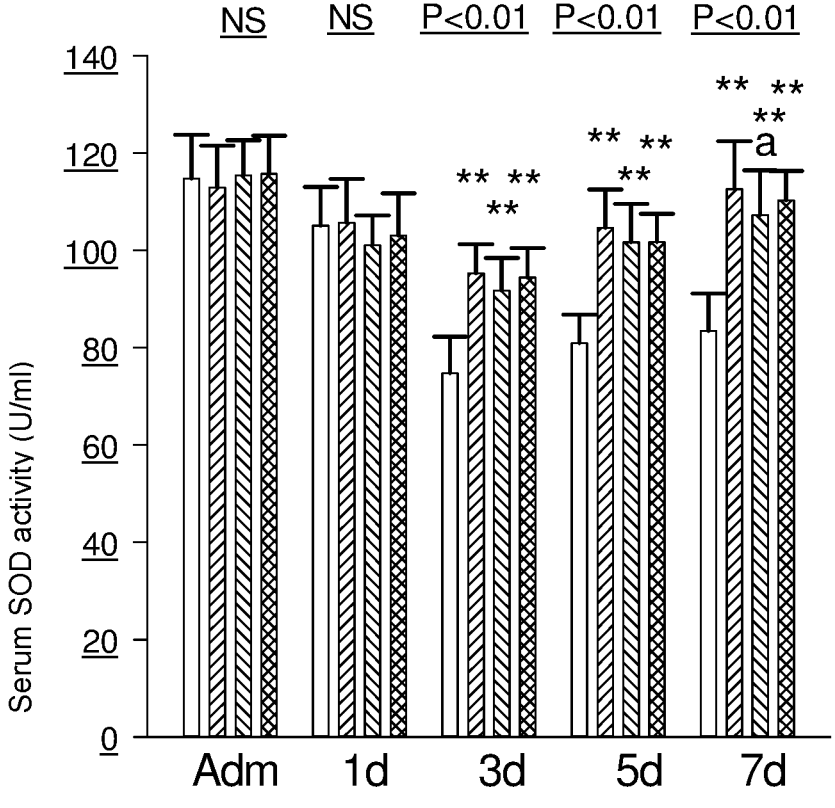
Figure 3H:
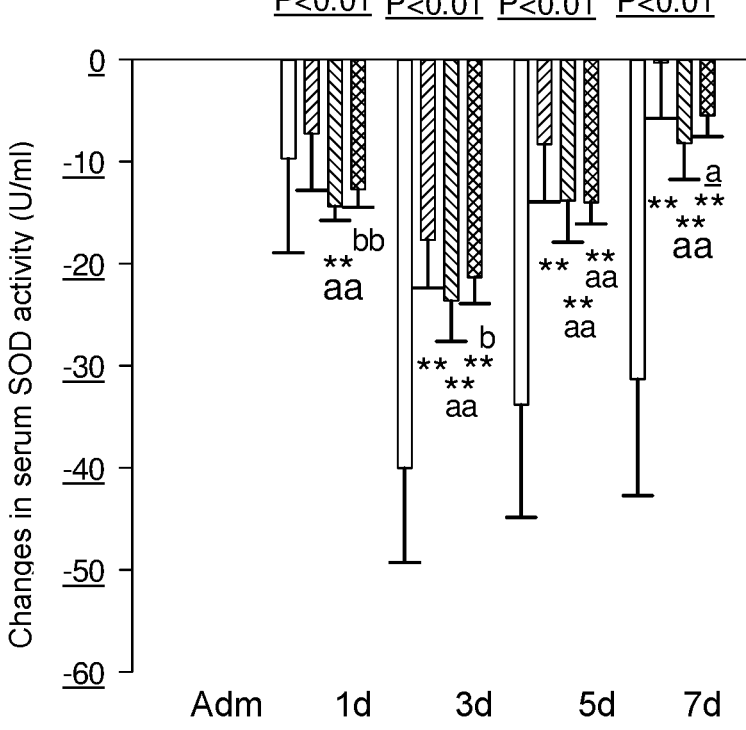
Figure 3I:
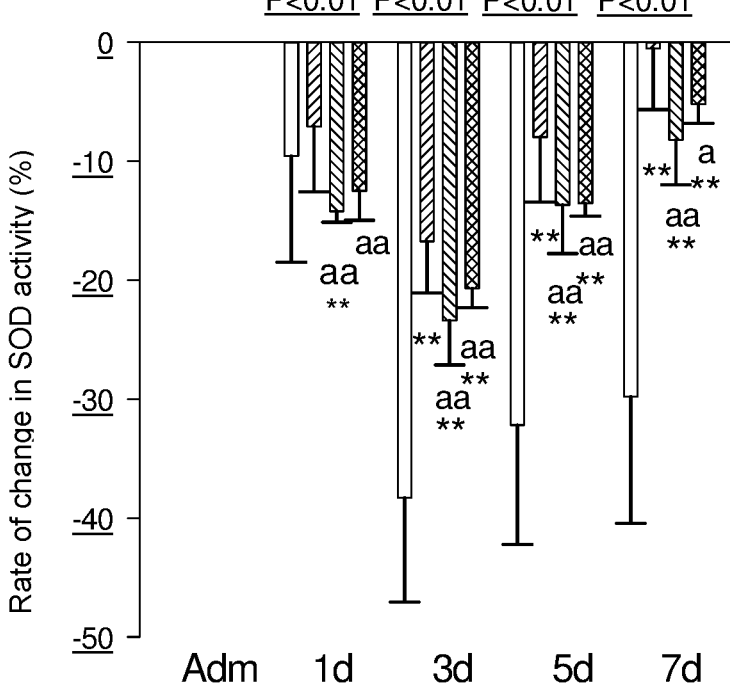
Figure 3I:
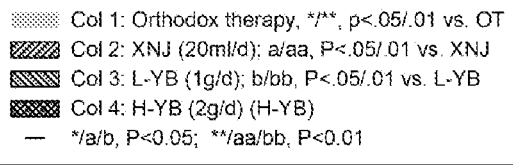

The present disclosure involves the demonstration by repeated-measure analysis and ANOVA analysis of serum S100B concentration as an indicator of secondary brain injury that shows significantly better efficacy of YB and XNJ Treatment than OT (P<0.001), Time (P<0.001) and Time× Treatment interaction (P<0.001) on S100B. Serum S100B concentration increased rapidly after craniotomy in all groups and peaked on Days 3 before S100B fell more rapidly and became significantly lower (P<0.01) in the XNJ, I-YB and h-YB groups than in the OT group on Days 3, 5 and 7 (Tables 2 & 3, FIGS. 2 & 3). The rate of change (%) in serum S100B concentration was significantly greater (P<0.05) in I-YB group than in OT group on Day 1 post-surgery, and significantly greater (P<0.01) in the OT group than in XNJ and h-YB groups on Day 3 post-surgery whereas the absolute reduction and percentage reduction in serum S100B level were significantly greater in XNJ, I-YB and h-YB groups than in OT group since Day 5 post-surgery. On Day 7 post-surgery, S100B declined to 20.5%, 20.1% and 24.7% below baselines in the XNJ, I-YB, h-YB groups, respectively whereas it remained 19.4% above baseline in OT group.

The present disclosure involves the demonstration that YB and XNJ interventions resulted in significantly better acute recovery and long-term improvements in clinical prognosis and functional recovery. Further, the high dose of YB resulted in significant (rate) increases in GCS score than I-YB and XNJ 3 days post-surgery, suggesting more effective intervention after high dose YB administration whereas XNJ therapy resulted in more consistent and significantly less (rate of) reduction in SOD activity than YB, indicating a greater antioxidative potential of XNJ than YB. The relatively greater loss in SOD activity in I-YB group than in h-YB group on Day 1 and 3 and a great rate of increase in S100B in I-YB than XNJ on Day 3, indicating a dose-dependent neuroprotection of YB, possibly related to the multi anti-hemorrhage, anti-hemostasis and anti-inflammation properties of YB as discussed below.

6

Figure 1:
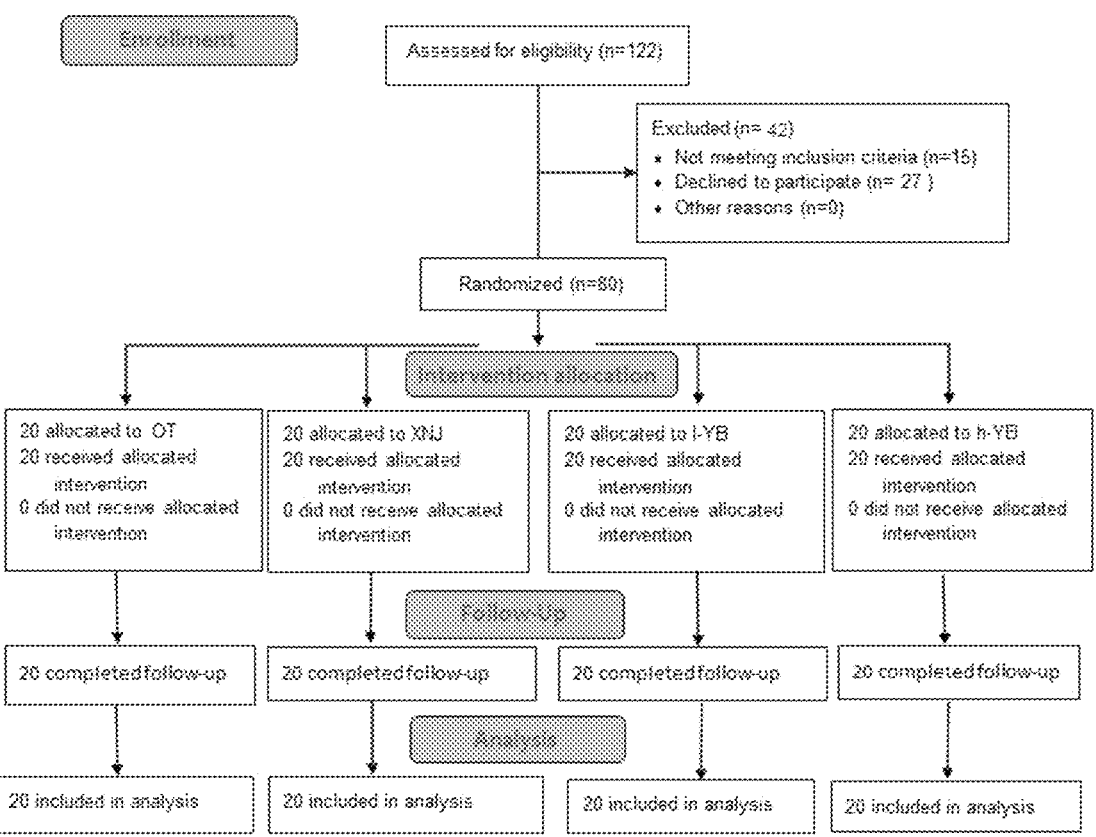
FIG. 1 is the flow diagram of the patient enrollment, intervention and follow up.

The present disclosure involves the demonstration of the use of a 4-arm parallel, randomized controlled trial design that involves 80 severity-matched TBI patients as depicted in the flow chart of enrollment randomization and experimental procedure (FIG. 1).

The practice of the current disclosure has employed, unless otherwise indicated, conventional clinical methodology of orthodox therapies, traditional medicine and ethnic medicine in the management of patients with acute TBI and craniotomy within the skill of the art. Such techniques are explained fully in the literature. (e.g.: The Guideline for the management of patients with severe TBI (Neurosurgery. 2017 Jan. 1; 80(1):6-15), Dai, C., Liang, Y., Hao, H., Z heng, X., Xie, L., Guan, T., Zhou, Y., Wang, G., 2013. Global detection and identification of components from Yunnan Bai yao based onliquid chromatography hybridiontraptime-of-flight mass spectrometry. J. Sep. Sci. 36, 1935-1944.

Einav, S., Y. Shoshan, H. Ovadia, I. Matot, M. Hersch, and E. Itshayek. 2006. Early postoperative serum S100 beta levels predict ongoing brain damage after meningioma surgery: a prospective observational study. Crit Care 10(5):R141.

Glass, N. E., A. Vadlamani, F. Hwang, Z. C. Sifri, A. Kunac, S. Bonne, S. R. Pentakota, P. Yonclas, A. C. Mosenthal, D. H. Livingston, and J. S. Albrecht. 2019. Bleeding and Thromboembolism After Traumatic Brain Injury in the Elderly: A Real Conundrum. J Surg Res 235:615-620.

Ladas, E. J., Karlik, J. B., Rooney, D., Taromina, K., Ndao, D. H., Granowetter, L., Kelly, K. M., 2012. Topical Yunnan Baiyao administration as an adjunctive therapy for bleeding complications in adolescents with advanced cancer. Support. Care Cancer 20, 3379-3383;

Tang, Z. L., X. Wang, B. Yi, Z. L. Li, C. Liang, and X. X. Wang. 2009. Effects of the preoperative administration of Yunnan Baiyao capsules on intraoperative blood loss in bimaxillary orthognathic surgery: a prospective, randomized, double-blind, placebo-controlled study. Int J Oral Maxillofac Surg 38(3):261-266;

Wang, J. C., Q. H. Wang, and J. X. Tian. 2015. Therapeutic effect of integrated traditional Chinese and Western medicine on patients with mental disorders caused by traumatic brain injury. Chin. J. Pract. Nerv. Dis. 18(8):50-52;

Xu, M., W. Su, Q. P. Xu, and W. D. Huang. 2010. Effect of Xingnaojing injection on cerebral edema and blood-brain barrier in rats following traumatic brain injury. Chin J Traumatol 13(3):158-162;

Xu, D., P. Huang, Z. Yu, D. H. Xing, S. Ouyang, and G. Xing. 2014. Efficacy and Safety of *Panax notoginseng* Saponin Therapy for Acute Intracerebral Hemorrhage, Meta-Analysis, and Mini Review of Potential Mechanisms of Action. Front Neurol 5:274;

Xu, Y. M., X. C. Wang, S. J. Zhang, T. T. Xu, H. Y. Li, S. Y. Hei, Z. H. Wen, Y. Z. Ma, Q. Wang, and W. X. Liang. 2018. Role of Xingnaojing combined with naloxone in treating intracerebral haemorrhage: A systematic review and meta-analysis of randomized controlled trials. Medicine (Baltimore) 97(43):e12967.

At admission, all TBI patients underwent complete medical history inquiry, physical examination, routine laboratory tests and cranial CT scan. The demographic and general clinical diagnosis at admission include scoring, degree of Glasgow Coma Scale (GCS), type and cause of injury, and type of craniotomy. Emergency craniotomy included intracranial hematoma evacuation, inactivated brain tissue resection, bone flap decompression and so on.

The inclusion criteria of the participants include:

1) diagnosed with moderate-to-severe TBI (within 12 hours of TBI, Glasgow Coma Scale score, 3-12), without apparent injury to other organs;

2) intracranial contusion/laceration, intracranial/epidural/subdural hematoma and other organic lesions confirmed by computed tomography (CT);

3) between 15 and 65 years of age; 4) received emergency craniotomy within 12 hours of TBI.

4) The patients or all their legal guardians gave their informed written consent.

The exclusion criteria of the participants include:

1) severe multiple or combined injuries;

2) history of severe chronic illness;

3) participated in any drug trial one month prior to this trial;

4) had malignant tumor or other diseases in the nervous or immune systems;

5) pregnant and lactating women;

6) with more than 400 ml blood transfusion during treatment;

7) uncooperative;

8) automatic discharge or death during the assessing phase;

9) had a second craniotomy;

10) history of allergy to YB or intravenous XNJ.

All study procedures were conducted in accordance with the Helsinki Declaration of 1975, in adherence to CONSORT guidelines (consort-statement.org/), and were approved by the Ethics Committee of the conducting hospital. The clinical trial was registered at Chinese Clinical Trial Registry (ChiCTR2000030280 and ChiMCTR2000003057).

Randomization

After craniotomy, TBI patients (N=80) were randomly assigned to one (n=20) of the four following treatments for 7 days by the clinicians using a predetermined randomization code generated by a random number generator (G.B.) according to the time order of admission: 1) orthodox treatment (OT); 2) OT plus Xingnaojing (XNJ)(intravenous drip of 20 ml Xingnaojing in 500 ml normal saline, daily, Wuxi Jimin Xinshanhe Pharmaceutical Co., Ltd., China); 3) OT plus low dose Yunnan Baiyao (I-YB) (1,000 mg, q.i.d) (Yunnan Baiyao Group Co., Ltd., China, oral or via stomach tube, q.i.d.); 4) OT plus high dose YB (h-YB) (2,000 mg, q.i.d). Orthodox treatments (OT) include dehydration, hemostasis, diuresis, prophylactic dose of antibiotics, hormone therapy, prevention of epilepsy and other necessary symptomatic treatments. Medical treatment was administered daily by caring nurses. Changes in clinical symptoms including vital signs, conscious state, pupil changes, etc. were scored daily.

The present disclosure involves the primary outcomes measures of the therapeutic effects of OT, YB and XNJ of TBI and craniotomy including measures of changes in postoperative scores of Glasgow Coma Scale (GCS) and post-discharge scores of Glasgow Outcome Scale (GOS) and Karnofsky Performance Scale (KPS) evaluated by trained neurologists. The GCS was used to evaluate disturbance of consciousness with eye opening, speech condition and motor response (mild=13-15, moderate=8-12, severe=3-7). The outcome of GOS was classified as good (4-5), bad (2-3) and death (1). KPS reflects changes in physical strength, functional rehabilitation and the abilities of daily life and work. A score of >80-points indicates independent, adequate capability of self-care in daily life; a score of 60-70 points indicate semi-dependent in daily life and a score of <60-points indicates lack of self-care capability.

The present disclosure involves the measures of the secondary brain injury biomarkers of the TBI patients including the changes in serum S100B protein and serum superoxide dismutase (SOD) activity. Five ml of venous blood was drawn on admission and on postoperative Days 1,3,5, and 7. After 2000 r/min centrifugation, the serum was stored at $-80°$ C., and thawed at $4°$ C. overnight before assaying. Serum S100B was determined by an enzyme-linked immunosorbent assay (Elisa) kit for human serum S100B protein (Randy D Company, USA) and serum superoxide dismutase (SOD) activity was determined by pyrogallol autoxidation method (PAM) using the SOD detection kit (Fujian Fuyuan Biotechnology Co., Ltd., China).

Methods of OT, YB and XNJ Administration and Delivery Forms: The present disclosure involves the oral administration or alternative stomach tubing administration of YB capsule (250 mg/each, a proprietary product of Yunnan Baiyao Group Co., Ltd. Yunnan, China). The present disclosure involves the intravenously drip administration of Xingnaojing (XNJ) (20 ml XNJ in 500 ml normal saline, XNJ is a trademark product of Wuxi Jimin Xinshanhe Pharmaceutical Co., Ltd., Wuxi, China).

The present disclosure involves orthodox treatments (OT) of TBI patients including dehydration, hemostasis, diuresis, prophylactic dose of antibiotics, hormone therapy, prevention of epilepsy and other necessary symptomatic treatments. Medical treatment was administered daily by hospital nurses. Changes in clinical symptoms including vital signs, conscious state, pupil changes, etc. are scored daily by trained neurologists.

Dosages of YB and XNJ Administration

Low dose of Yunnan Baiyao (l-YB), 1,000 mg/day, q.i.d, (oral or via stomach tube) High dose of Yunnan Baiyao (h-YB), 2,000 mg/day, q.i.d, (oral or via stomach tube) Xingnaojing (XNJ) 20 ml Xingnaojing in 500 ml normal saline (intravenous drip)

Participant sample size of this disclosure was estimated to be 20 participants per group or a total of 80 participants for the 4-arm trial when GCS scores were chosen as the main outcomes, with a designed power of 0.9, and assuming no baseline difference in GCS scores (8.0 for all groups) and assuming that after 7-days of OT and OT+YBY/XNJ interventions it would result in a 2-unit difference in mean GCS score between OT (10.0) and each of other 3 groups (12.0) with a standard deviation of 1.6. Similarly, if assuming 20 differences in mean GOS score outcome and 15 in standard deviation between the OT group (40.0) and the treatment groups (60.0) after 30 days of emergency craniotomy discharge, the minimal sample size would be 17 participants per treatment group or a total of 68 participants.

Normally distribution of GCS, S100B, SOD, GOS and KPS were confirmed and the data of GCS, S100B, SOD, GOS and KPS was presented. General linear model of repeated measures was performed to measure the effects of treatments, time and treatment*time interactions. Changes and change rate (%) of the measured variables at each postoperative observation time over the baseline (on admission) were analyzed using independent t-tests, ANOVA or nonparametric Mann-Whitney U-test as appropriate (SPSS 24, USA). Categorical variables were tested with $\chi^2$-test. Pearson correlations between the variables were calculated. A two-tailed P value <0.05 was considered statistically significant.

Traffic accident was the main cause of TBI and brain contusion was the primary damage type in this study (Table 1). There were no baseline differences in demographic and clinical characteristics including age, gender, GCS score, type and cause of TBI and type of craniotomy between the four treatment groups: OT, XNJ+OT, I-YB+OT, and h-YB+OT.

Repeated measure analysis showed significant effects of treatment (P<0.001), time (P<0.001) and time×treatment interaction (P<0.001) and a trend effect of treatment (P=0.2) on GCS scores observed during the first 7-day period post craniotomy that were confirmed by ANOVA (Table 2, FIGS. 2 & 3A-3C). GCS score was lowest at admission in all groups but improved more quickly and became significantly greater in XNJ, I-YB, h-YB groups than in OT group since Day 3 (P<0.01). The improvement rate in GCS were significantly greater in h-YB than in I-YB and XNJ groups on Days 3, 5 and 7 (P<0.01, all) which may also reflex a relatively lower baseline GCS value in the h-YB group (7.30±2.43) than in OT, XNJ and I-YB groups (8.10±2.38, 8.60±2.50, 8.50±2.48, respectively).

Repeated measure analysis and ANOVA analysis showed significant effects of treatment (P<0.001) and time (P<0.001) but no time×treatment interactions (P<0.001) on the mean scores of GOS and KPS which improved in all treatment groups after 1 and 3 Months of craniotomy, albeit with the XNJ, I-YB and h-YB groups showing consistent better clinical prognosis than the OT group (P<0.01, all). GOS and KPS scores were similar between XNJ, I-YB and h-YB groups (P>0.05) (Table 2, FIG. 2). One month after craniotomy the scores of GOS (3.80±0.95, 3.70±0.57, 3.70±0.87) and KPS (62.50±20.49, 59.50±10.99, 58.50±17.25) in the XNJ, I-YB, h-YB groups were 27.5%-31% and 50%-60% significantly greater than that in OT group (2.90±1.07 and 39.00±21.25) (P<0.01, all), respectively. Similar differences remained 3 months after surgery.

Serum S100B and SOD Repeated measure analysis and ANOVA showed significant effects of Treatment (P<0.001), Time (P<0.001) and Time×Treatment interaction (P<0.001) on serum S100B concentration that increased rapidly after surgery and peaked in all groups on Days 3 before fell more rapidly and became significantly lower (P<0.01) in the XNJ, I-YB and h-YB groups than in the OT group on Days 3, 5 and 7 (Tables 2, FIGS. 2B & 3D-3F). The rate of change (%) in serum S100B was significantly greater (P<0.05) in I-YB than in OT group on Day 1 of the treatment, and significantly greater (P<0.01) in the OT group than in XNJ and h-YB groups on Day 3 of the treatment whereas reduction and percentage reduction in serum S100B level was significantly greater in XNJ, I-YB and h-YB groups than in OT group since Day 5 of treatment. On Day 7, S100B declined to 20.5%, 20.1% and 24.7% below baselines in the XNJ, I-YB, h-YB groups, respectively whereas it remained 19.4% above baseline in OT group.

Prediction of long-term TBI outcomes based on correlations between experimental variables: GCS score was significantly correlated with GOS/KPS scores in pooled TBI patients and in each of the treatment groups (P<0.01) (Table 3), indicating a predict value of postoperative recovery during the acute phase of post-surgery on long-term clinical prognosis of TBI. It is noticed that the correlation between GOS/KPS and GCS scores improved progressively from Day 1 till Day 7 after surgery. However, the reduced level of correlation between most variables immediately after the surgery (Day 1) indicates a disruptive effect of craniotomy. Serum S100B levels were negatively correlated with GCS/GOS/KPS scores in pooled patients and in each treatment group (Table 3). This and other analysis suggest that a higher S100B level on admission day or on Day 7 are better predictors of poor TBI outcomes (low GCS/GOS/KPS scores). In contrast, serum SOD activity was positively correlated with GCS/GOS/KPS scores (P<0.01) in the pooled and in the 3 co-treatment groups but not in the OT group. Similarly, SOD level on postoperative Day 7 is a better predictor of GCS/GOS/KPS scores than SOD on other days in the pooled and 3 adjuvant treatment groups but not the OT group. Our data suggest that GCS and SOD are positive predictors and S100B is a negative predictor of clinical prognosis.

The present disclosure demonstrates that Yunnan Baiyao (YB) and Xingnaojing (XNJ) were more effective than orthodox therapies for patients with mild-to-moderate TBI and craniotomy. The present disclosure addresses the urgent need for innovative therapies for acute TBI and craniotomy especially in emergency situations and situations of limited resources. In the present disclosure, both YB and XNJ treatments resulted in similar significant improvements in neuroprotection and clinical prognosis. However, some differences do exist. The h-YB resulted in significant (rate of) increases in GCS score than I-YB and XNJ three days after surgery, suggesting more effective intervention after high dose YB administration whereas XNJ therapy resulted in more consistent and significantly less (rate of) reduction in SOD activity than YB, indicating a greater antioxidative potential of XNJ than YB. The greater loss in SOD activity in I-YB group than in h-YB group on Day 1 and 3 and a great rate of increase in S100B in I-YB than XNJ on Day 3, indicating a dose-dependent neuroprotection of YB, possibly related to the multi anti-hemorrhage, anti-hemostasis and anti-inflammation properties of YB.

The present disclosure methods pertain to the development of novel therapies for treatment and prevention of coagulopathy and secondary neural injury-associated neurodegeneration and neuroinflammation diseases, including TBI, spinal cord injury, stroke, brain tumor, ischemic and hemorrhage stroke that may involve neurosurgery or craniotomy.

All references cited in the present disclosure are incorporated by reference in their entirety.

REFERENCES

Anderson, R. E., L. O. Hansson, O. Nilsson, R. Dijlai-Merzoug, and G. Settergren. "High Serum S100b Levels for Trauma Patients without Head Injuries." *Neurosurgery* 48, no. 6 (June 2001): 1255-8; discussion 58-60. dx.doi.org/10.1097/00006123-200106000-00012.

Arcaroli, J. J., J. E. Hokanson, E. Abraham, M. Geraci, J. R. Murphy, R. P. Bowler, C. A. Dinarello, L. Silveira, J. Sankoff, D. Neyland, P. Wischmeyer, and J. D. Crapo. "Extracellular Superoxide Dismutase Haplotypes Are Associated with Acute Lung Injury and Mortality." *Am J Respir Crit Care Med* 179, no. 2 (Jan. 15, 2009): 105-12. dx.doi.org/10.1164/rccm.200710-1566OC.

Berger, R. P., M. C. Pierce, S. R. Wisniewski, P. D. Adelson, R. S. Clark, R. A. Ruppel, and P. M. Kochanek. "Neuron-Specific Enolase and S100b in Cerebrospinal Fluid after Severe Traumatic Brain Injury in Infants and Children." *Pediatrics* 109, no. 2 (February 2002): E31. dx.doi.org/10.1542/peds.109.2.e31.

Berger, R. P., M. C. Pierce, S. R. Wisniewski, P. D. Adelson, and P. M. Kochanek. "Serum S100b Concentrations Are Increased after Closed Head Injury in Children: A Preliminary Study." *J Neurotrauma* 19, no. 11 (November 2002): 1405-9. dx.doi.org/10.1089/089771502320914633.

Bokesch, P. M., E. Appachi, M. Cavaglia, E. Mossad, and R. B. Mee. "A Glial-Derived Protein, S100b, in Neonates and Infants with Congenital Heart Disease: Evidence for Preexisting Neurologic Injury." *Anesth Analg* 95, no. 4 (October 2002): 889-92, table of contents. dx.doi.org/10.1097/00000539-200210000-00018.

Cheng, Y., J. Zan, Y. Song, G. Yang, H. Shang, and W. Zhao. "Evaluation of Intestinal Injury, Inflammatory Response and Oxidative Stress Following Intracerebral Hemorrhage in Mice." *Int J Mol Med* 42, no. 4 (October 2018): 2120-28. dx.doi.org/10.3892/ijmm.2018.3755.

Clark, R. S., H. Bayir, C. T. Chu, S. M. Alber, P. M. Kochanek, and S. C. Watkins. "Autophagy Is Increased in Mice after Traumatic Brain Injury and Is Detectable in Human Brain after Trauma and Critical Illness." *Autophagy* 4, no. 1 (January 2008): 88-90. ncbi.nlm.nih.gov/pubmed/17957135.

Clark, R. S., J. Chen, S. C. Watkins, P. M. Kochanek, M. Chen, R. A. Stetler, J. E. Loeffert, and S. H. Graham. "Apoptosis-Suppressor Gene Bcl-2 Expression after Traumatic Brain Injury in Rats." *J Neurosci* 17, no. 23 (Dec. 1, 1997): 9172-82. ncbi.nlm.nih.gov/pubmed/9364064.

Clark, R. S., P. M. Kochanek, P. D. Adelson, M. J. Bell, J. A. Carcillo, M. Chen, S. R. Wisniewski, K. Janesko, M. J. Whalen, and S. H. Graham. "Increases in Bcl-2 Protein in Cerebrospinal Fluid and Evidence for Programmed Cell Death in Infants and Children after Severe Traumatic Brain Injury." *J Pediatr* 137, no. 2 (August 2000): 197-204. dx.doi.org/10.1067/mpd.2000.106903.

Clark, R. S., P. M. Kochanek, C. E. Dixon, M. Chen, D. W. Marion, S. Heineman, S. T. DeKosky, and S. H. Graham. "Early Neuropathologic Effects of Mild or Moderate Hypoxemia after Controlled Cortical Impact Injury in Rats." *J Neurotrauma* 14, no. 4 (April 1997): 179-89. dx.doi.org/10.1089/neu.1997.14.179.

Cox, A. L., A. J. Coles, J. Nortje, P. G. Bradley, D. A. Chatfield, S. J. Thompson, and D. K. Menon. "An Investigation of Auto-Reactivity after Head Injury." *J Neuroimmunol* 174, no. 1-2 (May 2006): 180-6. dx.doi.org/10.1016/j.jneuroim.2006.01.007.

Einav, S., Y. Shoshan, H. Ovadia, I. Matot, M. Hersch, and E. Itshayek. "Early Postoperative Serum S100 Beta Levels Predict Ongoing Brain Damage after Meningioma Surgery: A Prospective Observational Study." *Crit Care* 10, no. 5 (2006): R141. dx.doi.org/10.1186/cc5058.

Forbes, M. L., R. S. Clark, C. E. Dixon, S. H. Graham, D. W. Marion, S. T. DeKosky, J. K. Schiding, and P. M. Kochanek. "Augmented Neuronal Death in Ca3 Hippocampus Following Hyperventilation Early after Controlled Cortical Impact." *J Neurosurg* 88, no. 3 (March 1998): 549-56. dx.doi.org/10.317/jns.1998.88.3.0549.

Hutchinson, P. J., M. T. O'Connell, N. J. Rothwell, S. J. Hopkins, J. Nortje, K. L. Carpenter, I. Timofeev, P. G. Al-Rawi, D. K. Menon, and J. D. Pickard. "Inflammation in Human Brain Injury: Intracerebral Concentrations of Il-1alpha, Il-1beta, and Their Endogenous Inhibitor Il-1ra." *J Neurotrauma* 24, no. 10 (October 2007): 1545-57. dx.doi.org/10.1089/neu.2007.0205.

Juul, K., A. Tybjaerg-Hansen, S. Marklund, N. H. Heegaard, R. Steffensen, H. Sillesen, G. Jensen, and B. G. Nordestgaard. "Genetically Reduced Antioxidative Protection and Increased Ischemic Heart Disease Risk: The Copenhagen City Heart Study." *Circulation* 109, no. 1 (Jan. 6, 2004): 59-65. dx.doi.org/10.1161/01.CIR.0000105720.28086.6C.

Kim, G. W., T. Kondo, N. Noshita, and P. H. Chan. "Manganese Superoxide Dismutase Deficiency Exacerbates Cerebral Infarction after Focal Cerebral Ischemia/Reperfusion in Mice: Implications for the Production and Role of Superoxide Radicals." *Stroke* 33, no. 3 (March 2002): 809-15. dx.doi.org/10.1161/hs0302.103745.

Knoblach, S. M., M. Nikolaeva, X. Huang, L. Fan, S. Krajewski, J. C. Reed, and A. I. Faden. "Multiple Caspases Are Activated after Traumatic Brain Injury: Evidence for Involvement in Functional Outcome." *J Neurotrauma* 19, no. 10 (October 2002): 1155-70. dx.doi.org/10.1089/08977150260337967.

Kobylecki, C. J., S. Afzal, and B. G. Nordestgaard. "Genetically Low Antioxidant Protection and Risk of Cardiovascular Disease and Heart Failure in Diabetic Subjects." *EBioMedicine* 2, no. 12 (December 2015): 2010-5. dx.doi.org/10.1016/j.ebiom.2015.11.026.

Kontos, H. A. and E. P. Wei. "Superoxide Production in Experimental Brain Injury." *J Neurosurg* 64, no. 5 (May 1986): 803-7. dx.doi.org/10.3171/jhs.1986.645.0803.

Lee, B., J. Leem, H. Kim, H. G. Jo, S. H. Yoon, A. Shin, J. U. Sul, Y. Y. Choi, Y. Yun, and C. Y. Kwon. "Herbal Medicine for Acute Management and Rehabilitation of Traumatic Brain Injury: A Protocol for a Systematic Review." *Medicine* (Baltimore) 98, no. 3 (January 2019): e14145. dx.doi.org/10.1097/MD.0000000000014145.

Li, D. R., B. L. Zhu, T. Ishikawa, D. Zhao, T. Michiue, and H. Maeda. "Immunohistochemical Distribution of S-100 Protein in the Cerebral Cortex with Regard to the Cause of Death in Forensic Autopsy." *Leg Med* (Tokyo) 8, no. 2 (March 2006): 78-85. dx.doi.org/10.1016/j.legalmed.2005.09.002.

Loane, D. J., B. A. Stoica, and A. I. Faden. "Neuroprotection for Traumatic Brain Injury." *Handb Clin Neurol* 127 (2015): 343-66. dx.doi.org/10.1016/B978-0-444-52692-6.00022-2.

Lu, G., L. Zhu, X. Wang, H. Zhang, and Y. Li. "Decompressive Craniectomy for Patients with Traumatic Brain Injury: A Pooled Analysis of Randomized Controlled Trials." *World Neurosurg* 133 (January 2020): e135-e48. dx.doi.org/10.1016/j.wneu.2019.08.184.

Muir, J. K., M. Tynan, R. Caldwell, and E. F. Ellis. "Superoxide Dismutase Improves Posttraumatic Cortical Blood Flow in Rats." *J Neurotrauma* 12, no. 2 (April 1995): 179-88. dx.doi.org/10.1089/neu.1995.12.179.

Muller, P., D. Jirsch, J. D'Sousa, C. Kerr, and C. Knapp. "Gastrointestinal Bleeding after Craniotomy: A Retrospective Review of 518 Patients." *Can J Neurol Sci* 15, no. 4 (November 1988): 384-7. ncbi.nlm.nih.gov/pubmed/3208221.

Newcombe, V. F., G. B. Williams, J. Nortje, P. G. Bradley, D. A. Chatfield, J. G. Outtrim, S. G. Harding, J. P. Coles, B. Maiya, J. H. Gillard, P. J. Hutchinson, J. D. Pickard, T. A. Carpenter, and D. K. Menon. "Concordant Biology Underlies Discordant Imaging Findings: Diffusivity Behaves Differently in Grey and White Matter Post Acute Neurotrauma." *Acta Neurochir Suppl* 102 (2008): 247-51. ncbi.nlm.nih.gov/pubmed/19388324.

Papa, L., D. Edwards, and M. Ramia. "Exploring Serum Biomarkers for Mild Traumatic Brain Injury." In *Brain Neurotrauma: Molecular, Neuropsychological, and Rehabilitation Aspects*, edited by F. H. Kobeissy, Frontiers in Neuroengineering. Boca Raton (Fla.), 2015.

Petzold, A., A. J. Green, G. Keir, S. Fairley, N. Kitchen, M. Smith, and E. J. Thompson. "Role of Serum S100b as an Early Predictor of High Intracranial Pressure and Mortality in Brain Injury: A Pilot Study." *Crit Care Med* 30, no. 12 (December 2002): 2705-10. dx.doi.org/10.1097100003246-200212000-00015.

Qiu, W., C. Guo, H. Shen, K. Chen, L. Wen, H. Huang, M. Ding, L. Sun, Q. Jiang, and W. Wang. "Effects of Unilateral Decompressive Craniectomy on Patients with Unilateral Acute Post-Traumatic Brain Swelling after Severe Traumatic Brain Injury." *Crit Care* 13, no. 6 (2009): R185. dx.doi.org/10.1186/cc8178.

Raso Vasquez, A. O., M. D. Kertai, and M. L. Fontes. "Postoperative Thrombocytopenia: Why You Should Consider Antiplatelet Therapy?" *Curr Opin Anaesthesiol* 31, no. 1 (February 2018): 61-66. dx.doi.org/10.1097/ACO.0000000000000551.

Rothermundt, M., M. Peters, J. H. Prehn, and V. Arolt. "S100b in Brain Damage and Neurodegeneration." *Microsc Res Tech* 60, no. 6 (Apr. 15, 2003): 614-32. dx.doi.org/10.1002/jemt.10303.

Rutigliano, D., M. R. Egnor, C. J. Priebe, J. E. McCormack, N. Strong, R. J. Scriven, and T. K. Lee. "Decompressive Craniectomy in Pediatric Patients with Traumatic Brain Injury with Intractable Elevated Intracranial Pressure." *J Pediatr Surg* 41, no. 1 (January 2006): 83-7; discussion 83-7. dx.doi.org/10.1016/j.jpedsurg.2005.10.010.

Shim, H. K., S. H. Yu, B. C. Kim, J. H. Lee, and H. J. Choi. "Relationship between Clinical Outcomes and Superior Sagittal Sinus to Bone Flap Distance During Unilateral Decompressive Craniectomy in Patients with Traumatic Brain Injury: Experience at a Single Trauma Center." *Korean J Neurotrauma* 14, no. 2 (October 2018): 99-104. dx.doi.org/10.13004/kjnt.2018.14.2.99.

Simon, D. W., M. J. McGeachy, H. Bayir, R. S. Clark, D. J. Loane, and P. M. Kochanek. "The Far-Reaching Scope of Neuroinflammation after Traumatic Brain Injury." *Nat Rev Neurol* 13, no. 3 (March 2017): 171-91. dx.doi.org/10.1038/nrneurol.2017.13.

Steiner, J., H. G. Bernstein, H. Bielau, A. Berndt, R. Brisch, C. Mawrin, G. Keilhoff, and B. Bogerts. "Evidence for a Wide Extra-Astrocytic Distribution of S100b in Human Brain." *BMC Neurosci* 8 (Jan. 2, 2007): 2. dx.doi.org/10.1186/1471-2202-8-2.

Streitburger, D. P., K. Arelin, J. Kratzsch, J. Thiery, J. Steiner, A. Villringer, K. Mueller, and M. L. Schroeter. "Validating Serum S100b and Neuron-Specific Enolase as Biomarkers for the Human Brain—a Combined Serum, Gene Expression and Mri Study." *PLoS One* 7, no. 8 (2012): e43284. dx.doi.org/10.1371/journal.pone.0043284.

Su, T. M., C. M. Lan, T. H. Lee, S. W. Hsu, N. W. Tsai, and C. H. Lu. "Risk Factors for the Development of Posttraumatic Hydrocephalus after Unilateral Decompressive Craniectomy in Patients with Traumatic Brain Injury." *J Clin Neurosci* 63 (May 2019): 62-67. dx.doi.org/10.1016/j.jocn.2019.02.006.

Tapper, J., M. B. Skrifvars, R. Kivisaari, J. Siironen, and R. Raj. "Primary Decompressive Craniectomy Is Associated with Worse Neurological Outcome in Patients with Traumatic Brain Injury Requiring Acute Surgery." *Surg Neurol Int* 8 (2017): 141. dx.doi.org/10.4103/sni.sni_453_16.

Timofeev, I., M. Czosnyka, K. L. Carpenter, J. Nortje, P. J. Kirkpatrick, P. G. Al-Rawi, D. K. Menon, J. D. Pickard, A. K. Gupta, and P. J. Hutchinson. "Interaction between Brain Chemistry and Physiology after Traumatic Brain Injury: Impact of Autoregulation and Microdialysis Catheter Location." *J Neurotrauma* 28, no. 6 (June 2011): 849-60. dx.doi.org/10.1089/neu.2010.1656.

Timofeev, I., C. Dahyot-Fizelier, N. Keong, J. Nortje, P. G. Al-Rawi, M. Czosnyka, D. K. Menon, P. J. Kirkpatrick, A. K. Gupta, and P. J. Hutchinson. "Ventriculostomy for Control of Raised Icp in Acute Traumatic Brain Injury." *Acta Neurochir Suppl* 102 (2008): 99-104. ncbi.nlm.nih.gov/pubmed/19388297.

Timofeev, I., J. Nortje, P. G. Al-Rawi, P. J. Hutchinson, and A. K. Gupta. "Extracellular Brain Ph with or without Hypoxia Is a Marker of Profound Metabolic Derangement and Increased Mortality after Traumatic Brain Injury." *J Cereb Blood Flow Metab* 33, no. 3 (March 2013): 422-7. dx.doi.org/10.1038/jcbfm.2012.186.

Wang, J. C., Q. H. Wang, and J. X. Tian. "Therapeutic Effect of Integrated Traditional Chinese and Western 601 Medicine on Patients with Mental Disorders Caused by Traumatic Brain Injury." *Chin. J. Pract. Nerv. Dis.* 18, no. 8 (2015): 50-52.

Xing, Z., Z. Xia, W. Peng, J. Li, C. Zhang, C. Fu, T. Tang, J. Luo, Y. Zou, R. Fan, W. Liu, X. Xiong, W. Huang, C. Sheng, P. Gan, and Y. Wang. "Xuefu Zhuyu Decoction, a Traditional Chinese Medicine, Provides Neuroprotection in a Rat Model of Traumatic Brain Injury Via an Anti-Inflammatory Pathway." *Sci Rep* 6 (Jan. 28, 2016): 20040. dx.doi.org/10.1038/srep20040.

Yamada, H., Y. Yamada, T. Adachi, A. Fukatsu, M. Sakuma, A. Futenma, and S. Kakumu. "Protective Role of Extracellular Superoxide Dismutase in Hemodialysis Patients." *Nephron* 84, no. 3 (March 2000): 218-23. dx.doi.org/10.1159/000045580.

Yunoki, M., M. Kawauchi, N. Ukita, Y. Noguchi, S. Nishio, Y. Ono, S. Asari, T. Ohmoto, M. Asanuma, and N. Ogawa. "Effects of Lecithinized Superoxide Dismutase on Traumatic Brain Injury in Rats." *J Neurotrauma* 14, no. 10 (October 1997): 739-46. dx.doi.org/10.1089/neu.1997.14.739.

Zaghloul, N., H. Patel, C. Codipilly, P. Marambaud, S. Dewey, S. Frattini, P. T. Huerta, M. Nasim, E. J. Miller, and M. Ahmed. "Overexpression of Extracellular Superoxide Dismutase Protects against Brain Injury Induced by Chronic Hypoxia." *PLoS One* 9, no. 9 (2014): e108168. dx.doi.org/10.1371/journal.pone.0108168.

Zhang, X., Y. Chen, L. W. Jenkins, P. M. Kochanek, and R. S. Clark. "Bench-to-Bedside Review: Apoptosis/Programmed Cell Death Triggered by Traumatic Brain Injury." *Crit Care* 9, no. 1 (February 2005): 66-75. dx.doi.org/10.1186/cc.2950.

Zhou, M., R. Dominguez, and M. Baudry. "Superoxide Dismutase/Catalase Mimetics but Not Map Kinase Inhibitors Are Neuroprotective against Oxygen/Glucose Deprivation-Induced Neuronal Death in Hippocampus." *J Neurochem* 103, no. 6 (December 2007): 2212-23. dx.doi.org/10.1111/j.1471-4159.2007.04906.x.

TABLE 1

Clinical characteristics, GCS score, causes and subtypes of TBI of the participants at admission

| Characteristics/No. of cases | OT (n = 20) | XNJ (n = 20) | l-YB (n = 20) | h-YB (n = 20) | X² | P |
|---|---|---|---|---|---|---|
| Male:Female | 12:8 | 11:9 | 13:7 | 12:8 | 0.417 | 0.937 [a] |
| Age, y, mean(min-max) | 41.7 ± 10.54 | 43.1 ± 10.66 | 42.3 ± 14.05 | 42.3 ± 9.65 | 0.461 | 0.927 [b] |
| Degree of injury | | | | | | |
| Severe:Moderate | 10:10 | 8:12 | 8:12 | 12:8 | 2.020 | 0.568 [a] |
| Admission time (hours from injury) mean(min-max) | 4.7(1.5-8) | 5.3(2.5-12) | 4.8(2-7.5) | 5.1(2-8) | 0.59 | 0.899 [b] |
| Causes of TBI (N/%) | | | | | 3.628 | 0.989 [a] |
| Traffic accident | 9(45) | 7(35) | 7(35) | 8(40) | | |
| Falling | 4(20) | 5(25) | 4(20) | 3(15) | | |
| Blow | 5(25) | 3(15) | 4(20) | 4(20) | | |
| tumble | 2(10) | 3(15) | 3(15) | 3(15) | | |
| crush | 0(0) | 2(10) | 2(10) | 2(10) | | |
| Damage type (N/%) | | | | | 2 296 | 0.999 [a] |
| Epidural hematoma | 2(10) | 3(15) | 2(10) | 3(15) | | |
| Subdural hematoma | 5(25) | 6(30) | 6(30) | 4(20) | | |
| Brain contusion | 10(50) | 9(45) | 9(50) | 10(50) | | |
| Intracerebral hematoma | 2(10) | 1(5) | 1(5) | 1(5) | | |
| Multiple hematoma | 1(5) | 1(5) | 2(10) | 2(10) | | |
| Operation method (N/%) | | | | | | |
| Decompressive craniectomy | 12(60) | 8(40) | 9(45) | 11(55) | 2.000 | 0.572 [a] |
| Intracranial hematoma evacuation | 10(50) | 11(55) | 11(55) | 10(50) | 0.201 | 0.978 [a] |
| Inactivated brain tissue resection | 10(50) | 9(45) | 9(45) | 10(50) | 0.201 | 0.978 [a] |

[a] Chi-square Test;
[b] K Independent Samples test.
OT, Orthodox therapy group;
XNJ, OT + Xingnaojing group;
l-YB, OT + low-dose Yunnan Baiyao group;
h-YB, OT + high dose Yunnan Baiyao group

TABLE 2

Repeated measure analysis of Changes in GCS, S100B,
SOD, Glasgow Outcome Scale and Karnofsky Performance
Scale after emergency craniotomy in patients with
moderate-to severe TBI show significant differences
in therapeutic effects between OT, XNJ, I-YB and h-YB
and time * treatment interaction of, therapies

| No. of cases | Treatment F, P | Time F, P | Time * Treatment F, P |
|---|---|---|---|
| GCS (N, 80) | 1.57, 0.20 | 250.8, 0.00** | 6.16, 0.00** |
| S100B (N, 80) | 40.4, 0.000** | 1482.8, 0.00** | 27.3, 0.00** |
| SOD (N, 80) | 19.1, 0.000** | 456.1, 0.00** | 22.8, 0.00** |
| GOS (N,80) | 4.60, 0.005** | 138.6, 0.00** | 0.839, 0.477 |

TABLE 2-continued

Repeated measure analysis of Changes in GCS, S100B,
SOD, Glasgow Outcome Scale and Karnofsky Performance
Scale after emergency craniotomy in patients with
moderate-to severe TBI show significant differences
in therapeutic effects between OT, XNJ, I-YB and h-YB
and time * treatment interaction of, therapies

| No. of cases | Treatment F, P | Time F, P | Time * Treatment F, P |
|---|---|---|---|
| KPS (N, 80) | 7.04, 0.000** | 378.0, 0.00** | 0.489, 0.691 |

GCS, Glasgow Coma Scale
GOS, Glasgow Outcome Scale
KPS, Karnofsky Performance Scale
S100B, serum S100B level
SOD, serum superoxide dismutase activity
**P < 0.01, vs. different therapies, or vs. different observation time

TABLE 3

Changes in GCS, S100B, SOD, GOS and KPS in patients with moderate-to-severe TBI and craniotomy after orthodox therapy,
Xingnaojing, low and high doses of Yunnan Baiyao adjunct therapies (means ± SD)

| | | OT (n = 20) | | OT + XNJ (n = 20) | | OT + l-YB (n = 20) | | OT + h-YB (n = 20) | |
|---|---|---|---|---|---|---|---|---|---|
| | | | P [a] | | P [a], P [b] | | P [a], P [b] | | P [a], P [b] |
| | Days | | | | | | | | |
| GCS Score | Admission | 8.10 ± 2.38 | / | 8.60 ± 2.50 | /, 0.52 | 8.50 ± 2 48 | /, 0.61 | 7.30 ± 2.43 | /, 0.31 |
| | 1 | 8.20 ± 2.29 | 0.063 | 8.80 ± 2.33 | 0.059, 0.40 | 8.70 ± 2.16 | 0.061, 0.48 | 7.35 ± 2.16 | 0.057, 0.23 |
| | 3 | 8.30 ± 1.95 | 0.056 | 9.90 ± 2.00 | 0.018, 0.01 | 9.90 ± 1.97 | 0.016, 0.01 | 9.80 ± 1.77 | 0.022, 0.02 |
| | 5 | 9.35 ± 2.06 | 0.029 | 10.90 ± 1.58 | <0.001, 0.01 | 10.65 ± 1.69 | <0.001, 0.02 | 10.95 ± 1.43 | <0.001, <0.001 |
| | 7 | 10.10 ± 1.80 | 0.021 | 11.85 ± 1.93 | <0.001, <0.001 | 11.55 ± 1.70 | <0.001, 0.01 | 11.30 ± 1.53 | <0.001, 0.03 |

TABLE 3-continued

Changes in GCS, S100B, SOD, GOS and KPS in patients with moderate-to-severe TBI and craniotomy after orthodox therapy, Xingnaojing, low and high doses of Yunnan Baiyao adjunct therapies (means ± SD)

| | | | | | | | | | |
|---|---|---|---|---|---|---|---|---|---|
| S100B protein (µg/l) | Admission | 2.08 ± 0.14 | / | 1.99 ± 0.18 | 0.07 | 2.00 ± 0.15 | 0.11 | 2.00 ± 0.16 | 0.09 |
| | 1 | 2.74 ± 0.15 | | 2.67 ± 0.13 | 0.13 | 2.81 ± 0.14 | 0.11 | 2.73 ± 0.14 | 0.89 |
| | 3 | 3.38 ± 0.23 | | 2.99 ± 0.34 | <0.001 | 3.20 ± 0.32 | 0.05 | 3.12 ± 0.30 | 0.01 |
| | 5 | 2.84 ± 0.20 | | 1.83 ± 0.23 | <0.001 | 1.93 ± 0.29 | <0.001 | 1.94 ± 0.18 | <0.001 |
| | 7 | 2.48 ± 0.23 | | 1.57 ± 0.29 | <0.001 | 1.59 ± 0.23 | <0.001 | 1.51 ± 0.25 | <0.001 |
| Serum SOD activity (U/ml) | Admission | 114.80 ± 8.93 | / | 112.91 ± 8.61 | 0.47 | 115.44 ± 7.23 | 0.81 | 115.76 ± 7.77 | 0.71 |
| | 1 | 105.10 ± 7.95 | | 105.65 ± 9.03 | 0.83 | 101.06 ± 6.15 | 0.12 | 103.05 ± 8.67 | 0.42 |
| | 3 | 74.75 ± 7.51 | | 95.26 ± 6.00 | <0.001 | 91.79 ± 6.64 | <0.001 | 94.41 ± 6.07 | <0.001 |
| | 5 | 80.97 ± 5.85 | | 104.60 ± 7.89 | <0.001 | 101.64 ± 7.92 | <0.001 | 101.74 ± 5.82 | <0.001 |
| | 7 | 83.47 ± 7.71 | | 112.59 ± 9.83 | <0.001 | 107.24 ± 9.23 | <0.001 | 110.29 ± 6.05 | <0.001 |
| | Months | | | | | | | | |
| GOS Score | 1 | 2.90 ± 1.07 | / | 3.80 ± 0.95 | /, 0.00 | 3.70 ± 0.57 | /, 0.01 | 3.70 ± 0.87 | /, 0.01 |
| KPS Score | 3 | 3.65 ± 0.99 | / | 4.35 ± 0.81 | /, 0.01 | 4.45 ± 0.61 | /, <0.001 | 4.30 ± 0.80 | /, 0.01 |
| | 1 | 39.00 ± 12.25 | / | 62.50 ± 20.49 | /, <0.001 | 59.50 ± 10.99 | /, <0.001 | 58.50 ± 17.25 | /, <0.001 |
| | 3 | 57.00 ± 20.80 | / | 78.00 ± 18.53 | /, <0.001 | 77.50 ± 15.17 | /, <0.001 | 76.50 ± 17.55 | /, <0.001 |

Change in Score Score

| | | | | | | | | | |
|---|---|---|---|---|---|---|---|---|---|
| | Days | | | | | | | | |
| GCS score | 1 | 0.10 ± 0.85 | 0.063 | 0.20 ± 0.89 | 0.059, 0.72 | 0.20 ± 0.89 | 0.061, 0.72 | 0.05 ± 0.89 | 0.057, 0.86 |
| | 3 | 0.20 ± 1.36 | 0.056 | 1.30 ± 0.73 | 0.018, <0.001 | 1.40 ± 0.82 | 0.016, <0.001 | 2.50 ± 1.32 | 0.022, <0.001 |
| | 5 | 1.25 ± 0.79 | 0.029 | 2.30 ± 1.22 | <0.001, 0.003 | 2.15 ± 0.93 | <0.001, 0.01 | 3.65 ± 1.35 | <0.001, <0.001 |
| | 7 | 2.00 ± 0.86 | 0.021 | 3.25 ± 1.02 | <0.001, <0.001 | 3.05 ± 1.00 | <0.001, 0.002 | 4.00 ± 1.17 | <0.001, <0.001 |
| Change in S100B (µg/l) | 1 | 0.65 ± 0.17 | | 0.68 ± 0.19 | 0.57 | 0.80 ± 0.10 | 0.002 | 0.73 ± 0.09 | 0.09 |
| | 3 | 1.30 ± 0.18 | | 0.99 ± 0.29 | <0.001 | 1.19 ± 0.26 | 0.17 | 1.12 ± 0.21 | 0.02 |
| | 5 | 0.75 ± 0.19 | | −0.16 ± 0.25 | <0.001 | −0.07 ± 0.24 | <0.001 | −0.06 ± 0.16 | <0.001 |
| | 7 | 0.40 ± 0.23 | | −0.42 ± 0.33 | <0.001 | −0.42 ± 0.10 | <0.001 | −0.49 ± 0.13 | <0.001 |
| Change in SOD (U/ml) | 1 | −9.70 ± 9.24 | | −7.26 ± 5.54 | 0.17 | −14.38 ± 1.38 | 0.009 | −12.71 ± 12.63 | 0.09 |
| | 3 | −40.05 ± 9.22 | | −17.65 ± 4.72 | <0.001 | −23.65 ± 3.97 | <0.001 | −0.49 ± 2.56 | <0.001 |
| | 5 | −33.83 ± 11.04 | | −8.31 ± 5.62 | <0.001 | −13.80 ± 4.09 | <0.001 | −12.71 ± 2.07 | <0.001 |
| | 7 | −31.33 ± 11.44 | | −0.33 ± 5.42 | <0.001 | −8.20 ± 3.56 | <0.001 | −5.47 ± 2.07 | <0.001 |
| | Months | | | | | | | | |
| Change in GOS | 3 | 0.75 ± 0.44 | / | 0.55 ± 0.61 | /, 0.21 | 0.75 ± 0.44 | /, 1.00 | 0.60 ± 0.50 | /, 0.35 |
| Change in KPS | 3 | 18.00 ± 7.68 | / | 15.50 ± 8.26 | /, 0.33 | 18.00 ± 8.34 | /, 1.00 | 18.00 ± 7.68 | /, 1.00 |
| | Days | | | | | | | | |
| (%) Change in GCS | 1 | 1.98 ± 10.72 | 0.063 | 4.02 ± 12.20 | 0.059, 0.60 | 4.48 ± 11.93 | 0.061, 0.52 | 2.58 ± 13.73 | 0.057, 0.88 |
| | 3 | 5.29 ± 16.70 | 0.056 | 18.76 ± 15.55 | 0.018, 0.06 | 21.09 ± 20.46 | 0.016, 0.03 | 42.67 ± 32.53 | 0.022, <0 001 |
| | 5 | 18.31 ± 13.55 | 0.029 | 33.58 ± 27.70 | <0.001, 0.09 | 31.62 ± 25.15 | <0.001, 0.14 | 61.37 ± 39.55 | <0.001, <0.001 |
| | 7 | 29.47 ± 20.63 | 0.021 | 44.36 ± 28.26 | <0.001, 0.12 | 43.52 ± 30.33 | <0.001, 0.14 | 65.83 ± 38.00 | <0.001, <0.001 |
| (%) Change in S100B | 1 | 31.68 ± 9.41 | | 34.94 ± 12.50 | 0.26 | 40.43 ± 6.75 | 0.003 | 36.94 ± 6.58 | 0.07 |
| | 3 | 62.49 ± 9.51 | | 50.56 ± 15.97 | 0.004 | 59.71 ± 13.63 | 0.49 | 56.19 ± 9.98 | 0.12 |
| | 5 | 36.49 ± 9.82 | | −7.70 ± 13.02 | <0.001 | −3.73 ± 12.23 | <0.001 | −2.92 ± 7.97 | <0.001 |
| | 7 | 19.44 ± 11.29 | | −20.51 ± 16.17 | <0.001 | −21.12 ± 6.33 | <0.001 | −24.71 ± 8.24 | <0.001 |
| (%) Change in SOD | 1 | −9.56 ± 8.93 | | −7.08 ± 5.49 | 0.15 | −14.22 ± 0.92 | 0.008 | −12.50 ± 2.58 | 0.09 |
| | 3 | −38.30 ± 8.76 | | −16.73 ± 4.32 | <0.001 | −23.40 ± 3.71 | <0.001 | −20.71 ± 1.60 | <0.001 |
| | 5 | −32.22 ± 10.00 | | −7.99 ± 5.45 | <0.001 | −13.69 ± 4.10 | <0.001 | −13.55 ± 1.08 | <0.001 |
| | 7 | −29.81 ± 10.66 | | −0.52 ± 5.15 | <0.001 | −8.22 ± 3.75 | <0.001 | −5.20 ± 1.61 | <0.001 |
| | Months | | | | | | | | |
| (%) Change in GOS | 3 | 30.00 ± 19.76 | / | 17.50 ± 20.21 | /, 0.03 | 21.25 ± 13.10 | /, 0.12 | 18.33 ± 16.36 | /, 0.04 |
| (%) Change in KPS | 3 | 62.90 ± 43.30 | / | 29.93 ± 21.01 | /, <0.001 | 30.58 ± 14.56 | /, <0.001 | 34.65 ± 18.76 | /, 0.001 |

3 P [(a)], P values, compared with the value at admission
4 P [(b)], P values, compared with the value of OT

TABLE 4

| | | GCSa | GCS1 | GCS3 | GCS5 | GCS7 | GOS1 | GOS3 |
|---|---|---|---|---|---|---|---|---|
| | | Correlations between the acute and long-term variables of TBI | | | | | | |
| GCSa | Pearson Correlation | 1 | .936** | .835** | .835** | .875** | .689** | .685** |
| | Sig. (2-tailed) | 0.000 | 0.000 | 0.000 | 0.000 | 0.000 | 0.000 | 0.000 |
| | N | 80 | 80 | 80 | 80 | 80 | 80 | 80 |
| GCS1 | Pearson Correlation | .936** | 1 | .847** | .808** | .860** | .600** | .619** |
| | Sig. (2-tailed) | 0.000 | | 0.000 | 0.000 | 0.000 | 0.000 | 0.000 |
| | N | 80 | 80 | 80 | 80 | 80 | 80 | 80 |
| GCS3 | Pearson Correlation | .835** | .847** | 1 | .935** | .925** | .711** | .675** |
| | Sig. (2-tailed) | 0.000 | 0.000 | | 0.000 | 0.000 | 0.000 | 0.000 |
| | N | 80 | 80 | 80 | 80 | 80 | 80 | 80 |
| GCS5 | Pearson Correlation | .835** | .808** | .935** | 1 | .932** | .768** | .714** |
| | Sig. (2-tailed) | 0.000 | 0.000 | 0.000 | | 0.000 | 0.000 | 0.000 |
| | N | 80 | 80 | 80 | 80 | 80 | 80 | 80 |
| GCS7 | Pearson Correlation | .875** | .860** | .925** | .932** | 1 | .788** | .738** |
| | Sig. (2-tailed) | 0.000 | 0.000 | 0.000 | 0.000 | | 0.000 | 0.000 |
| | N | 80 | 80 | 80 | 80 | 80 | 80 | 80 |
| GOS1 | Pearson Correlation | .689** | .600** | .711** | .768** | .788** | 1 | .848** |
| | Sig. (2-tailed) | 0.000 | 0.000 | 0.000 | 0.000 | 0.000 | | 0.000 |
| | N | 80 | 80 | 80 | 80 | 80 | 80 | 80 |
| GOS3 | Pearson Correlation | .685** | .619** | .675** | .714** | .738** | .848** | 1 |
| | Sig. (2-tailed) | 0.000 | 0.000 | 0.000 | 0.000 | 0.000 | 0.000 | |
| | N | 80 | 80 | 80 | 80 | 80 | 80 | 80 |
| KPS1 | Pearson Correlation | .688** | .605** | .720** | .764** | .799** | .968** | .878** |
| | Sig. (2-tailed) | 0.000 | 0.000 | 0.000 | 0.000 | 0.000 | 0.000 | 0.000 |
| | N | 80 | 80 | 80 | 80 | 80 | 80 | 80 |
| KPS3 | Pearson Correlation | .694** | .614** | .713** | .758** | .781** | .877** | .962** |
| | Sig. (2-tailed) | 0.000 | 0.000 | 0.000 | 0.000 | 0.000 | 0.000 | 0.000 |
| | N | 80 | 80 | 80 | 80 | 80 | 80 | 80 |
| S100a | Pearson Correlation | −.354** | −.281* | −.398** | −.433** | −.434** | −.438** | −.412** |
| | Sig. (2-tailed) | 0.001 | 0.012 | 0.000 | 0.000 | 0.000 | 0.000 | 0.000 |
| | N | 80 | 80 | 80 | 80 | 80 | 80 | 80 |
| S1001 | Pearson Correlation | −.399** | −.316** | −.382** | −.401** | −.431** | −.396** | −.337** |
| | Sig. (2-tailed) | 0.000 | 0.004 | 0.000 | 0.000 | 0.000 | 0.000 | 0.002 |
| | N | 80 | 80 | 80 | 80 | 80 | 80 | 80 |
| S1003 | Pearson Correlation | −.324** | −.289** | −.353** | −.380** | −.376** | −.414** | −.387** |
| | Sig. (2-tailed) | 0.003 | 0.009 | 0.001 | 0.001 | 0.001 | 0.000 | 0.000 |
| | N | 80 | 80 | 80 | 80 | 80 | 80 | 80 |
| S1005 | Pearson Correlation | −0.146 | −0.125 | −.423** | −.419** | −.427** | −.456** | −.483** |
| | Sig. (2-tailed) | 0.197 | 0.269 | 0.000 | 0.000 | 0.000 | 0.000 | 0.000 |
| | N | 80 | 80 | 80 | 80 | 80 | 80 | 80 |
| S1007 | Pearson Correlation | −.333** | −.283* | −.567** | −.627** | −.630** | −.606** | −.535** |
| | Sig. (2-tailed) | 0.003 | 0.011 | 0.000 | 0.000 | 0.000 | 0.000 | 0.000 |
| | N | 80 | 80 | 80 | 80 | 80 | 80 | 80 |
| SODa | Pearson Correlation | .329** | .381** | .390** | .361** | .346** | .250* | 327** |
| | Sig. (2-tailed) | 0.003 | 0.000 | 0.000 | 0.001 | 0.002 | 0.025 | 0.003 |
| | N | 80 | 80 | 80 | 80 | 80 | 80 | 80 |

TABLE 4-continued

Correlations between the acute and long-term variables of TBI

| | | | | | | | | |
|---|---|---|---|---|---|---|---|---|
| SOD1 | Pearson Correlation | .335** | .347** | .324** | .28** | .313** | .270* | .249* |
| | Sig. (2-tailed) | 0.002 | 0.002 | 0.003 | 0.010 | 0.005 | 0.016 | 0.026 |
| | N | 80 | 80 | 80 | 80 | 80 | 80 | 80 |
| SOD3 | Pearson Correlation | 0.213 | .244* | .495** | .523** | .507** | .492** | .485** |
| | Sig. (2-tailed) | 0.058 | 0.029 | 0.000 | 0.000 | 0.000 | 0.000 | 0.000 |
| | N | 80 | 80 | 80 | 80 | 80 | 80 | 80 |
| SOD5 | Pearson Correlation | 0.189 | 0.192 | .436** | .455** | .478** | .477** | .418** |
| | Sig. (2-tailed) | 0.093 | 0.087 | 0.000 | 0.000 | 0.000 | 0.000 | 0.000 |
| | N | 80 | 80 | 80 | 80 | 80 | 80 | 80 |
| SOD7 | Pearson Correlation | .260* | .260* | .535** | .551** | .553** | .540** | .467** |
| | Sig. (2-tailed) | 0.020 | 0.020 | 0.000 | 0.000 | 0.000 | 0.000 | 0.000 |
| | N | 80 | 80 | 80 | 80 | 80 | 80 | 80 |

| | | KPS1 | KPS3 | S100a | S1001 | S1003 | S1005 | S1007 |
|---|---|---|---|---|---|---|---|---|
| GCSa | Pearson Correlation | .688** | .694** | −.354** | −.399** | .324** | −0.146 | −.333** |
| | Sig. (2-tailed) | 0.000 | 0.000 | 0.001 | 0.000 | 0.003 | 0.197 | 0.003 |
| | N | 80 | 80 | 80 | 80 | 80 | 80 | 80 |
| GCS1 | Pearson Correlation | .605** | .614** | −.281* | −.316** | −.289** | −0.125 | −.283* |
| | Sig. (2-tailed) | 0.000 | 0.000 | 0.012 | 0.004 | 0.009 | 0.269 | 0.011 |
| | N | 80 | 80 | 80 | 80 | 80 | 80 | 80 |
| GCS3 | Pearson Correlation | .720** | .713** | −.398** | −.382** | −.353** | −.423** | −.567** |
| | Sig. (2-tailed) | 0.000 | 0.000 | 0.000 | 0.000 | 0.001 | 0.000 | 0.000 |
| | N | 80 | 80 | 80 | 80 | 80 | 80 | 80 |
| GCS5 | Pearson Correlation | .764** | .758** | −.433** | −.401** | −.380** | −.419** | −.627** |
| | Sig. (2-tailed) | 0.000 | 0.000 | 0.000 | 0.000 | 0.001 | 0.000 | 0.000 |
| | N | 80 | 80 | 80 | 80 | 80 | 80 | 80 |
| GCS7 | Pearson Correlation | .799** | .781** | −434** | −.431** | −.376** | −.427** | −.630** |
| | Sig. (2-tailed) | 0.000 | 0.000 | 0.000 | 0.000 | 0.001 | 0.000 | 0.000 |
| | N | 80 | 80 | 80 | 80 | 80 | 80 | 80 |
| GOS1 | Pearson Correlation | .968** | .877** | −.438** | −.396** | −.414** | −.456** | −.606** |
| | Sig. (2-tailed) | 0.000 | 0.000 | 0.000 | 0.000 | 0.000 | 0.000 | 0.000 |
| | N | 80 | 80 | 80 | 80 | 80 | 80 | 80 |
| GOS3 | Pearson Correlation | .878** | .962** | −.412** | −.337** | −.387** | −.483** | −.535** |
| | Sig. (2-tailed) | 0.000 | 0.000 | 0.000 | 0.002 | 0.000 | 0.000 | 0.000 |
| | N | 80 | 80 | 80 | 80 | 80 | 80 | 80 |
| KPS1 | Pearson Correlation | 1 | .921** | −.487** | −.402** | −.446** | −.544** | −.655** |
| | Sig. (2-tailed) | | 0.000 | 0.000 | 0.000 | 0.000 | 0.000 | 0.000 |
| | N | 80 | 80 | 80 | 80 | 80 | 80 | 80 |
| KPS3 | Pearson Correlation | .921** | 1 | −.469** | −.355** | −.429** | −.527** | −.616** |
| | Sig. (2-tailed) | 0.000 | | 0.000 | 0.001 | 0.000 | 0.000 | 0.000 |
| | N | 80 | 80 | 80 | 80 | 80 | 80 | 80 |
| S100a | Pearson Correlation | −.487** | −.469** | 1 | .502** | .638** | .444** | .493** |
| | Sig. (2-tailed) | 0.000 | 0.000 | | 0.000 | 0.000 | 0.000 | 0.000 |
| | N | 80 | 80 | 80 | 80 | 80 | 80 | 80 |
| S1001 | Pearson Correlation | −.402** | −.355** | .502** | 1 | .405** | 0.200 | .314** |
| | Sig. (2-tailed) | 0.000 | 0.001 | 0.000 | | 0.000 | 0.075 | 0.005 |
| | N | 80 | 80 | 80 | 80 | 80 | 80 | 80 |

TABLE 4-continued

Correlations between the acute and long-term variables of TBI

| | | | | | | | | |
|---|---|---|---|---|---|---|---|---|
| S1003 | Pearson Correlation | −.446** | −.429** | .638** | .405** | 1 | .517** | .526** |
| | Sig. (2-tailed) | 0.000 | 0.000 | 0.000 | 0.000 | | 0.000 | 0.000 |
| | N | 80 | 80 | 80 | 80 | 80 | 80 | 80 |
| S1005 | Pearson Correlation | −.544** | −.527** | .444** | 0.200 | .517** | 1 | .810** |
| | Sig. (2-tailed) | 0.000 | 0.000 | 0.000 | 0.075 | 0.000 | | 0.000 |
| | N | 80 | 80 | 80 | 80 | 80 | 80 | 80 |
| S1007 | Pearson Correlation | −655** | −.616** | .493** | .314** | .526** | .810** | 1 |
| | Sig. (2-tailed) | 0.000 | 0.000 | 0.000 | 0.005 | 0.000 | 0.000 | |
| | N | 80 | 80 | 80 | 80 | 80 | 80 | 80 |
| SODa | Pearson Correlation | .230* | .336** | −0.027 | 0.039 | −0.037 | 0.015 | −0.057 |
| | Sig. (2-tailed) | 0.040 | 0.002 | 0.814 | 0.728 | 0.747 | 0.894 | 0.618 |
| | N | 80 | 80 | 80 | 80 | 80 | 80 | 80 |
| SOD1 | Pearson Correlation | .249* | .296** | 0.075 | −0.087 | 0.026 | 0.102 | 0.030 |
| | Sig. (2-tailed) | 0.026 | 0.008 | 0.510 | 0.442 | 0.818 | 0.367 | 0.790 |
| | N | 80 | 80 | 80 | 80 | 80 | 80 | 80 |
| SOD3 | Pearson Correlation | .532** | .561** | −.244* | −0.091 | −.396** | −.691** | −.718** |
| | Sig. (2-tailed) | 0.000 | 0.000 | 0.029 | 0.423 | 0.000 | 0.000 | 0.000 |
| | N | 80 | 80 | 80 | 80 | 80 | 80 | 80 |
| SOD5 | Pearson Correlation | .527** | .519** | −0.158 | −0.075 | −.304** | −.669** | −.709** |
| | Sig. (2-tailed) | 0.000 | 0.000 | 0.162 | 0.510 | 0.006 | 0.000 | 0.000 |
| | N | 80 | 80 | 80 | 80 | 80 | 80 | 80 |
| SOD7 | Pearson Correlation | .581** | .569** | −.224* | −0.154 | −.363** | −.695** | −.750** |
| | Sig. (2-tailed) | 0.000 | 0.000 | 0.046 | 0.172 | 0.001 | 0.000 | 0.000 |
| | N | 80 | 80 | 80 | 80 | 80 | 80 | 80 |

| | | | SODa | SOD1 | SOD3 | SOD5 | SOD7 |
|---|---|---|---|---|---|---|---|
| | GCSa | Pearson Correlation | .329** | .335** | 0.213 | 0.189 | .260* |
| | | Sig. (2-tailed) | 0.003 | 0.002 | 0.058 | 0.093 | 0.020 |
| | | N | 80 | 80 | 80 | 80 | 80 |
| | GCS1 | Pearson Correlation | .381** | .347** | .244* | 0.192 | .260* |
| | | Sig. (2-tailed) | 0.000 | 0.002 | 0.029 | 0.087 | 0.020 |
| | | N | 80 | 80 | 80 | 80 | 80 |
| | GCS3 | Pearson Correlation | .390** | .324** | .495** | .436** | .535** |
| | | Sig. (2-tailed) | 0.000 | 0.003 | 0.000 | 0.000 | 0.000 |
| | | N | 80 | 80 | 80 | 80 | 80 |
| | GCS5 | Pearson Correlation | .361** | .288** | .523** | .455** | .551** |
| | | Sig. (2-tailed) | 0.001 | 0.010 | 0.000 | 0.000 | 0.000 |
| | | N | 80 | 80 | 80 | 80 | 80 |
| | GCS7 | Pearson Correlation | .346** | .313** | .507** | .478** | .553** |
| | | Sig. (2-tailed) | 0.002 | 0.005 | 0.000 | 0.000 | 0.000 |
| | | N | 80 | 80 | 80 | 80 | 80 |
| | GOS1 | Pearson Correlation | .250* | .270* | .492** | .477** | .540** |
| | | Sig. (2-tailed) | 0.025 | 0.016 | 0.000 | 0.000 | 0.000 |
| | | N | 80 | 80 | 80 | 80 | 80 |
| | GOS3 | Pearson Correlation | .327** | .249* | .485** | .418** | .467** |
| | | Sig. (2-tailed) | 0.003 | 0.026 | 0.000 | 0.000 | 0.000 |
| | | N | 80 | 80 | 80 | 80 | 80 |

TABLE 4-continued

| | | Correlations between the acute and long-term variables of TBI | | | | |
|---|---|---|---|---|---|---|
| KPS1 | Pearson Correlation | .230* | .249* | .532** | .527** | .581** |
| | Sig. (2-tailed) | 0.040 | 0.026 | 0.000 | 0.000 | 0.000 |
| | N | 80 | 80 | 80 | 80 | 80 |
| KPS3 | Pearson Correlation | .336** | .296** | .561** | .519** | .569** |
| | Sig. (2-tailed) | 0.002 | 0.008 | 0.000 | 0.000 | 0.000 |
| | N | 80 | 80 | 80 | 80 | 80 |
| S100a | Pearson Correlation | −0.027 | 0.075 | −.244* | −0.158 | −.244* |
| | Sig. (2-tailed) | 0.814 | 0.510 | 0.029 | 0.162 | 0.046 |
| | N | 80 | 80 | 80 | 80 | 80 |
| S1001 | Pearson Correlation | 0.039 | −0.087 | −0.091 | −0.075 | −0.154 |
| | Sig. (2-tailed) | 0.728 | 0.442 | 0.423 | 0.510 | 0.172 |
| | N | 80 | 80 | 80 | 80 | 80 |
| S1003 | Pearson Correlation | −0.037 | 0.026 | −.396** | −.304** | −.363** |
| | Sig. (2-tailed) | 0.747 | 0.818 | 0.000 | 0.006 | 0.001 |
| | N | 80 | 80 | 80 | 80 | 80 |
| S1005 | Pearson Correlation | 0.015 | 0.102 | −.691** | −.669** | −.695** |
| | Sig. (2-tailed) | 0.894 | 0.367 | 0.000 | 0.000 | 0.000 |
| | N | 80 | 80 | 80 | 80 | 80 |
| S1007 | Pearson Correlation | −0.057 | 0.030 | −.718** | −.709** | −.750** |
| | Sig. (2-tailed) | 0.618 | 0.790 | 0.000 | 0.000 | 0.000 |
| | N | 80 | 80 | 80 | 80 | 80 |
| SODa | Pearson Correlation | 1 | .719** | .421** | .344** | .364** |
| | Sig. (2-tailed) | | 0.000 | 0.000 | 0.002 | 0.001 |
| | N | 80 | 80 | 80 | 80 | 80 |
| SOD1 | Pearson Correlation | .719** | 1 | .405** | .385** | .365** |
| | Sig. (2-tailed) | 0.000 | | 0.000 | 0.000 | 0.001 |
| | N | 80 | 80 | 80 | 80 | 80 |
| SOD3 | Pearson Correlation | .421** | .405** | 1 | .904** | .926** |
| | Sig. (2-tailed) | 0.000 | 0.000 | | 0.000 | 0.000 |
| | N | 80 | 80 | 80 | 80 | 80 |
| SOD5 | Pearson Correlation | .344** | .385** | .904** | 1 | .928** |
| | Sig. (2-tailed) | 0.002 | 0.000 | 0.000 | | 0.000 |
| | N | 80 | 80 | 80 | 80 | 80 |
| SOD7 | Pearson Correlation | .364** | .365** | .926** | .928** | 1 |
| | Sig. (2-tailed) | 0.001 | 0.001 | 0.000 | 0.000 | |
| | N | 80 | 80 | 80 | 80 | 80 |

What is claimed is:

1. A method of treating a patient recovering from emergency craniotomy due to moderate-to-severe traumatic brain injury (TBI) comprising administering to the patient both orthodox therapy (OT) and a therapeutically effective amount of Yunnan Baiyao (YB) for seven consecutive days in an intensive care setting, wherein in comparison to patients receiving OT alone:

acute postoperative neurological recovery of the patient is improved as measured by Glasgow Coma Scale (GCS) during postoperative days 1, 3, 5, and 7;

long-term functional outcome of the patient is improved as measured by Glasgow Outcome Scale (GOS) and Karnofsky Performance Status (KPS) at 30 and 90 days; and secondary-injury biomarkers are modulated by reducing serum S100B levels and preserving or restoring serum superoxide dismutase (SOD) activity.

2. The method of claim 1, wherein the patient meets the following criteria:

(a) a GCS of 3-12 within 12 hours of TBI;

(b) computed tomography (CT)-confirmed intracranial lesion;

(c) age 15-65 years; and (d) emergency craniotomy within 12 hours of TBI occurrence.

3. The method of claim 1, wherein the orthodox therapy comprises one or more of dehydration therapy, hemostasis, diuresis, prophylactic antibiotics, hormone therapy, seizure prophylaxis, and supportive care, with daily monitoring of vital signs, consciousness, and pupil reactivity.

4. The method of claim 1, wherein the craniotomy comprises hematoma evacuation, resection of nonviable tissue, bone-flap decompression, or a combination thereof.

5. The method of claim 1, wherein said administering YB comprises administering 1,000 mg/day of the YB orally or via stomach tube for 7 days at a rate of four 250 mg doses every 3 hours.

6. The method of claim 1, wherein said administering YB comprises administering 2,000 mg/day of the YB orally or via stomach tube for 7 days at a dosage rate of four 500 mg doses every 3 hours.

7. The method of claim 1, wherein, by day 7, the patient exhibits at least a two-point improvement in GCS over baseline and improvement in at least one of GOS or KPS at 30 or 90 days compared with OT alone.

\* \* \* \* \*